US012565646B2

(12) United States Patent
Chatterjee et al.

(10) Patent No.: US 12,565,646 B2
(45) Date of Patent: Mar. 3, 2026

(54) ENHANCED PLATFORMS FOR UNNATURAL AMINO ACID INCORPORATION IN MAMMALIAN CELLS

(71) Applicant: TRUSTEES OF BOSTON COLLEGE, Chestnut Hill, MA (US)

(72) Inventors: Abhishek Chatterjee, Lexington, MA (US); Rachel E. Kelemen, Newton, MA (US); Delilah Jewel, Chestnut Hill, MA (US)

(73) Assignee: TRUSTEES OF BOSTON COLLEGE, Chestnut Hill, MA (US)

( * ) Notice: Subject to any disclaimer, the term of this patent is extended or adjusted under 35 U.S.C. 154(b) by 977 days.

(21) Appl. No.: 17/620,887

(22) PCT Filed: Jun. 19, 2020

(86) PCT No.: PCT/US2020/038766
§ 371 (c)(1),
(2) Date: Dec. 20, 2021

(87) PCT Pub. No.: WO2020/257668
PCT Pub. Date: Dec. 24, 2020

(65) Prior Publication Data
US 2022/0372467 A1        Nov. 24, 2022

Related U.S. Application Data

(60) Provisional application No. 62/864,570, filed on Jun. 21, 2019.

(51) Int. Cl.
| | |
|---|---|
| *C12N 15/67* | (2006.01) |
| *C12N 15/10* | (2006.01) |
| *C12N 15/86* | (2006.01) |
| *C12P 21/02* | (2006.01) |

(52) U.S. Cl.
CPC ......... *C12N 15/1058* (2013.01); *C12N 15/67* (2013.01); *C12N 15/86* (2013.01); *C12P 21/02* (2013.01); *C12N 2750/14122* (2013.01); *C12N 2750/14143* (2013.01); *C12Y 601/01026* (2013.01)

(58) Field of Classification Search
CPC ........ C12N 15/11; C12N 9/22; C12N 15/102; C12N 15/70; C12N 15/09; C12N 9/104; C12N 15/74; C12N 9/1241; C12N 9/127; C12Y 601/01026; C07K 2319/00
USPC ....................................... 435/69.1
See application file for complete search history.

(56) References Cited

U.S. PATENT DOCUMENTS

2016/0251336 A1    9/2016  Yang et al.

FOREIGN PATENT DOCUMENTS

| | | |
|---|---|---|
| AU | 2008301614 A1 | 3/2009 |
| CN | 101511856 A | 8/2009 |
| CN | 101528914 A | 9/2009 |
| CN | 102827827 A | 12/2012 |
| CN | 107012121 A | 8/2017 |
| CN | 107022568 A | 8/2017 |
| CN | 107177593 A | 9/2017 |
| CN | 110172467 A | 8/2019 |
| JP | 2010506591 A | 3/2010 |
| WO | WO 2006110182 A2 | 10/2006 |
| WO | WO 2009099073 A1 | 8/2009 |
| WO | WO2014140347 A2 | 9/2014 |

OTHER PUBLICATIONS

Davos et al., Proteins: Structure, Function and Genetics, 2000, vol. 41: 98-107.*
Wristlock et al., Quarterly Reviews of Biophysics , 2003, vol. 36 (3): 307-340.*
Kwiatkowski et al., Biochemistry, 1999, 38:11643-11650.*
Kisselev L., Structure, 2002, vol. 10: 8-9.*
Wu, N. et al., "A Genetically Encoded Photocaged Amino Acid," J. Am. Chem. Soc., 126(44):14306-14307 (2004).
Zheng, Y. et al., "Expanding the scope of single and dual noncanonical amino acid mutagenesis in mammalian cells using orthogonal polyspecific leucyl-tRNA synthetases," Biochemistry, 57(4):441-445 (2018). 11 pages.
Zheng, Y. et al., "Virus-Enabled Optimization and Delivery of the Genetic Machinery for Efficient Unnatural Amino Acid Mutagenesis in Mammalian Cells and Tissues," ACS Synth. Biol., 6:13-18 (2017).
International Preliminary Report on Patentability, issued Dec. 21, 2021, from International Application No. PCT/US2020/038766, filed on Jun. 19, 2020. 11 pages.
Erickson, S.B., et al., "Precise Photoremovable Pertubation of a Virus-Host Interaction," Angew. Chem. Int. Ed., 56: 4234-4237 (2017).
Fan, C., et al., "Rationally Evolving tRNA Pyl for Efficient Incorporation of Noncanonical Amico Acids," Nucleic Acid Research, 43(22): e156-e156 (2015).
International Search Report and Written Opinion of the International Searching Authority, mailed on Nov. 16, 2020, from International Application No. PCT/US2020/038766, filed on Jun. 19, 2020. 21 pages.
Invitation to Pay Additional Fees and Partial International Search, mailed on Sep. 22, 2020, from International Application No. PCT/US2020/038766, filed on Jun. 19, 2020. 12 pages.
Kelemen, R.C., et al. "A Precise Chemical Strategy to Alter the Receptor Specificity of the Adeno-Associated Virus," Angew. Chem. Int. Ed., 55: 10645-10649 (2016).

(Continued)

*Primary Examiner* — Tekchand Saidha
*Assistant Examiner* — Mohammad Y Meah
(74) *Attorney, Agent, or Firm* — HoustonHogle LLP

(57) ABSTRACT

The present invention involves the ability to 1) use a virus assisted directed evolution platform to significantly improve the activity of engineered nonsense-suppressor tRNAs in mammalian cells, 2) provide mutants of archaeal pyrrolysyl and *E. coli* leucyl tRNAs that show remarkably improved Uaa incorporation efficiency in mammalian cells, and 3) use these tRNAs to express recombinant proteins in mammalian cells incorporating Uaas at significantly improved yields.

23 Claims, 20 Drawing Sheets

Specification includes a Sequence Listing.

(56) References Cited

OTHER PUBLICATIONS

Kelemen, R.E., et al., "Synthesis at the Interface of Virology and Genetic Code Expansion," Current Opinion in Chemical Biology, 46: 164-171 (2018).

Meineke, B., et al., "Methanomethylophilus alvus Mx1201 Provides Basis for Mutual Orthogonal Pyrrolysyl tRNA/Aminoacyl-tRNA Synthetase Pairs in Mammalian Cells," ACS Chem. Biol. 13: 3087-3096 (2018).

Simon, A.J., et al., "Synthetic Evolution," Nature Biotechnology, 37: 730-743 (2019).

Tharp, J.M., et al., tRNAPyl: Structure, Function, and Applications, RNA Biol., 15(4-5): 441-452 (2018).

First Office Action received for Chinese Patent Application No. 202080045420.5, mailed on Apr. 30, 2024. 10 Pages.

Notice of Reasons for Refusal received for Japanese Patent Application No. 2021-574260, mailed on Jun. 18, 2024. 12 pages.

Search Report received for Japanese Patent Application No. 2021-574260, mailed on Jun. 12, 2024. 63 pages.

Kim, H., et al., "An Azido-Biotin Reagent for Use in the Isolation of Protein Adducts of Lipid-derived Electrophiles by Streptavidin Catch and Photorelease", Molecular & Cellular Proteomics 8.9, vol. 8 (9): 2080-2089 pages (2009).

Examiner requisition received for Canadian Patent Application No. 3,143,506, mailed on Mar. 6, 2024. 3 pages.

Esvelt, K. M. et al. "A system for the continuous directed evolution of biomolecules", Nature, 472(7344): 499-503 (2011).

Maheshri, N. et al. "Directed evolution of adeno-associated virus yields enhanced gene delivery vectors", Nature Biotechnology, 24(2): 198-204 (2006).

Third Office Action received for Chinese Patent Application No. 202080045420.5, mailed on Mar. 7, 2025.

Serfling, R. et al., "Designer tRNAs for efficient incorporation of non-canonical amino acids by the pyrrolysine system in mammalian cells", Nucleic Acids Research, 46(1): 1-10 pages (2017).

Second Office Action received for Chinese Patent Application No. 202080045420.5, mailed on Oct. 17, 2024. 13 pages.

Lin, S. et al. "Site-Specific Engineering of Chemical Functionalities on the Surface of Live Hepatitis D Virus", Angew. Chem. Int. Ed, 52:13970-13974 (2013).

Jewel, D. et al., "Virus-assisted directed evolution of enhanced suppressor tRNAs in mammalian cells", Nature Methods, vol. 20, Jan. 2023. 38 pages.

Decision of Rejection received for Japanese Application No. 2021-574260, mailed on Nov. 26, 2024. 17 pages.

Pre-Appeal Report received for Japanese Application No. 2021-574260, mailed on Apr. 24, 2025. 4 pages.

Fourth Office Action received for Chinese Patent Application No. 202080045420.5, mailed on May 6, 2025. 9 pages.

Rejection Decision received for Chinese Application No. 202080045420.5, mailed on Jul. 21, 2025. 11 pages.

Notice to Submit Response received for Korean Application No. 1020227002220, mailed on Aug. 26, 2025. 8 pages.

* cited by examiner

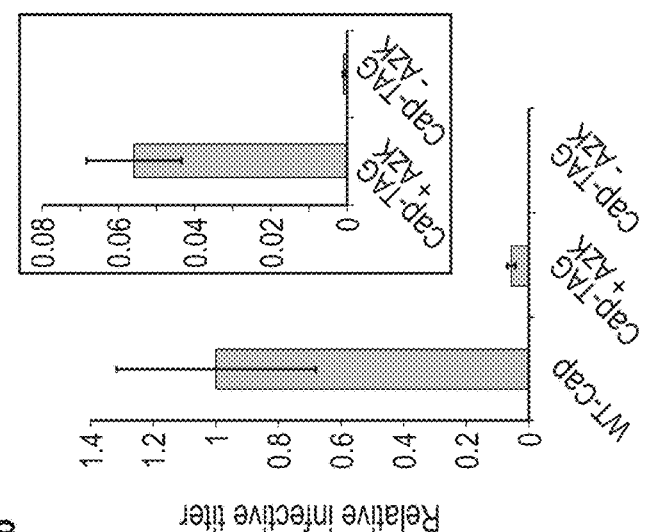
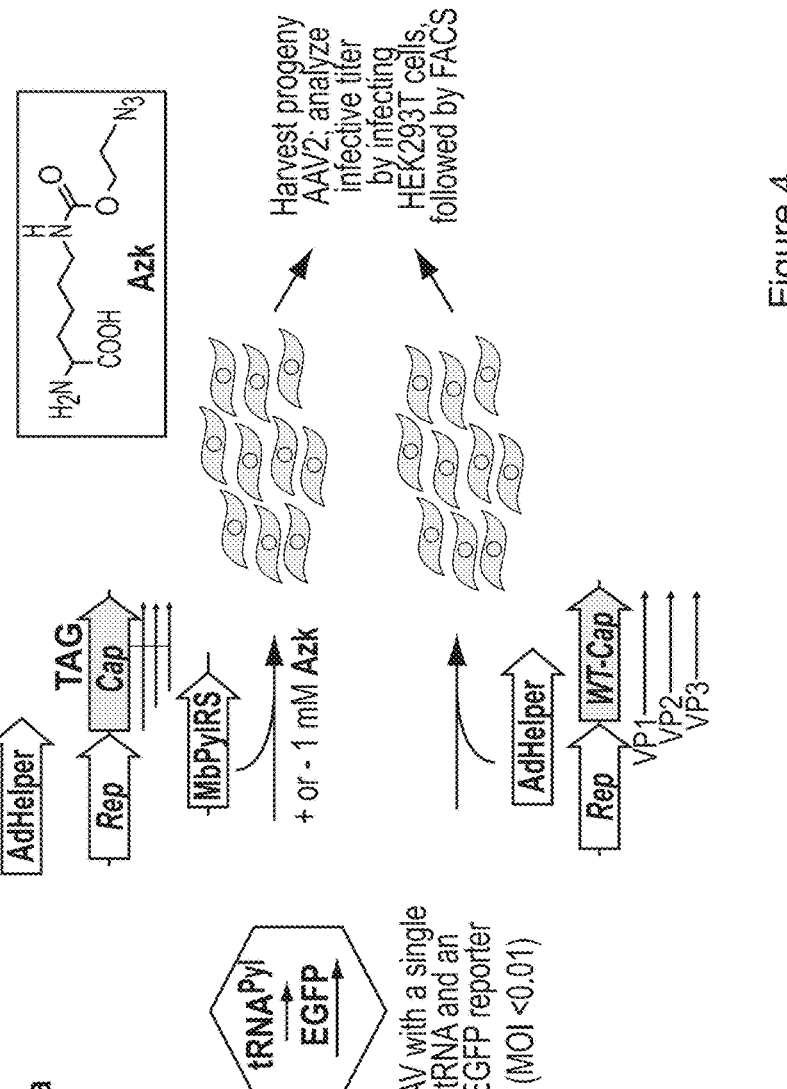
Figure 4 a
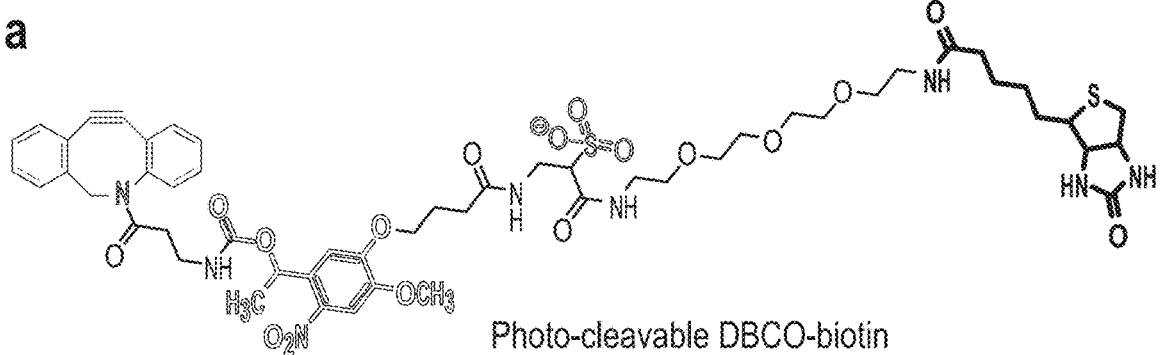
Photo-cleavable DBCO-biotin
b
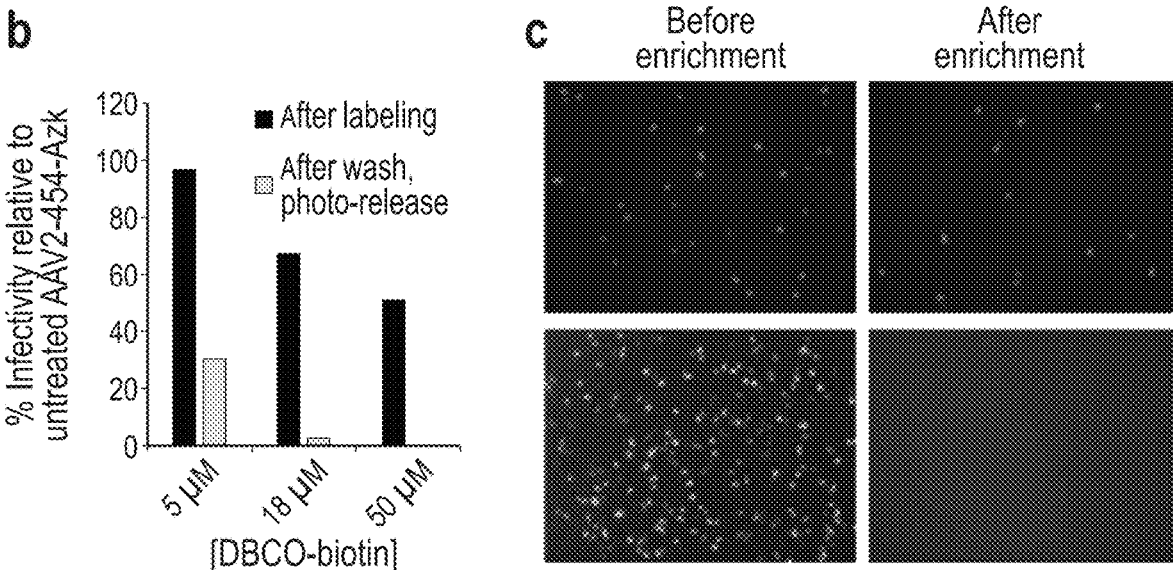
Figure 5

Before selection        After step 1        After step 2

1 : 10000        1 : 44        3 : 1

| A1 | 5 | 6 | 7 | 62 | 63 | 64 | | A2 | 2 | 3 | 4 | 65 | 66 | 67 |
|---|---|---|---|---|---|---|---|---|---|---|---|---|---|---|
| Wild-type | A | C | C | G | G | U | | Wild-type | G | A | A | U | U | C |
| GGG/CCU | G | G | G | C | C | U | | GGG/CCU | G | G | G | C | C | U |
| GGG/CCC | G | G | G | C | C | C | | GGG/UCU | G | G | G | U | C | U |
| GGG/UCC | G | G | G | U | C | C | | AGC/GCU | A | G | C | G | C | U |
| GGC/GCC | G | G | C | G | C | C | | UGG/UCA | U | G | G | U | C | A |
| GGG/CUC | G | G | G | C | U | C | | AAC/GUU | A | A | C | G | U | U |
| GGU/ACC | G | G | U | A | C | C | | AUG/CAU | A | U | G | C | A | U |
| AGG/UCU | A | G | G | U | C | U | | ACU/AGU | A | C | U | A | G | U |
| GCU/AGC | G | C | U | A | G | C | | ACU/GGU | A | C | U | G | G | U |
| CGG/CCG | C | G | G | C | C | G | | UGU/ACA | U | G | U | A | C | A |
| CCU/GGG | C | C | U | G | G | G | | UGU/GCA | U | G | U | G | C | A |
| CCU/AGG | C | C | U | A | G | G | | GUG/UGC | G | U | G | U | G | C |
| GGA/UUC | G | G | A | U | U | C | | AAG/UUU | A | A | G | U | U | U |
| UGG/CCA | U | G | G | C | C | A | | GCA/UGU | G | C | A | U | G | U |
| GCG/CGU | G | C | G | C | G | U | | CAU/GUG | C | A | U | G | U | G |
| AAC/GUU | A | A | C | G | U | U | | UCG/UGG | U | C | G | U | G | G |
| ACA/UGU | A | C | A | U | G | U | | AAA/UUU | A | A | A | U | U | U |
| UAC/GUA | U | A | C | G | U | A | | | | | | | | |
| GUG/CAC | G | U | G | C | A | C | | | | | | | | |
| UUG/CAA | U | U | G | C | A | A | | | | | | | | |
| | | | | | | | | | | | | | | |
| T1 | 45 | 46 | 47 | 59 | 60 | 61 | | T2 | 48 | 49 | 55 | 56 | 57 | 58 |
| Wild-type | C | C | G | C | G | G | | Wild-type | G | G | U | U | C | C |
| CCA/UGG | C | C | A | U | G | G | | GG/UACC | G | G | U | A | C | C |
| CAG/CUG | C | A | G | C | U | G | | GG/UGCC | G | G | U | G | C | C |
| CGG/CCG | C | G | G | C | C | G | | AG/UGCU | A | G | U | G | C | U |
| ACG/CGU | A | C | G | C | G | U | | UC/AAGG | U | C | A | A | G | G |
| CGC/GCG | C | G | C | G | C | G | | GU/UGAU | G | U | U | G | A | U |
| GUU/GAC | G | U | U | G | A | C | | | | | | | | |
| GGG/UCU | G | G | G | U | C | U | | | | | | | | |

Figure 9 a   EcLtR:
GCCCGGATGGTGGAATCGGTAGACACAAGGGATTCTAAATCCCTC
GGCGTTCGCGCTGTGCGGGTTCAAGTCCCGCTCCGGGTACCA b   EcLtR-h1:
GCCCGGATGGTGGAATCGGTAGACACAAGGGACTCTAAATCCCTC
GGCGTTCGCGCTGTGCGGGTTCAAGTCCCGCTCCGGGCACCA c

Figure 18

Sequence of AAV2 Cap (VP1), SEQ ID NO: 46:

```
MAADGYLPDWLEDTLSEGIRQWWKLKPGPPPPKPAERHKDDSRGLVLPGYKYLGPFNGLD
KGEPVNEADAAALEHDKAYDRQLDSGDNPYLKYNHADAEFQERLKEDTSFGGNLGRAVFQ
AKKRVLEPLGLVEEPVKTAPGKKRPVEHSPVEPDSSSGTGKAGQQPARKRLNFGQTGDAD
SVPDPQPLGQPPAAPSGLGTNTMATGSGAPMADNNEGADGVGNSSGNWHCDSTWMGDRVI
TTSTRTWALPTYNNHLYKQISSQSGASNDNHYFGYSTPWGYFDFNRFHCHFSPRDWQRLI
NNNWGFRPKRLNFKLFNIQVKEVTQNDGTTTIANNLTSTVQVFTDSEYQLPYVLGSAHQG
CLPPFPADVFMVPQYGYLTLNNGSQAVGRSSFYCLEYFPSQMLRTGNNFTFSYTFEDVPF
HSSYAHSQSLDRLMNPLIDQYLYYLSRTNTPSGTTTQSRLQFSQAGASDIRDQSRNWLPG
PCYRQQRVSKTSADNNNSEYSWTGATKYHLNGRDSLVNPGPAMASHKDDEEKFFPQSGVL
IFGKQGSEKTNVDIEKVMITDEEEIRTTNPVATEQYGSVSTNLQRGNRQAATADVNTQGV
LPGMVWQDRDVYLQGPIWAKIPHTDGHFHPSPLMGGFGLKHPPPQILIKNTPVPANPSTT
FSAAKFASFITQYSTGQVSVEIEWELQKENSKRWNPEIQYTSNYNKSVNVDFTVDTNGVY
SEPRPIGTRYLTRNL
```

Figure 20

ENHANCED PLATFORMS FOR UNNATURAL AMINO ACID INCORPORATION IN MAMMALIAN CELLS

RELATED APPLICATIONS

This application is a § 371 National Phase Application of International Application No. PCT/US2020/038766. filed on Jun. 19, 2020, which claims the benefit under 35 U.S.C. § 119 (e) of U.S. Provisional Application No. 62/864,570, filed on Jun. 21, 2019, both of which are incorporated herein by reference in their entirety.

GOVERNMENT SUPPORT

This invention was made with government support under grant numbers R01 GM124319 and R35 GM136437 awarded by the National Institutes of Health and grant number MCB1817893 awarded by the National Science Foundation. The government has certain rights in the invention.

INCORPORATION BY REFERENCE OF MATERIAL IN ASCII TEXT FILE

This application incorporates by reference the Sequence Liking contained in the following ASCII text file:

File name: 0342_0008WO1 txt; created Jun. 19, 2020, 17,574 bytes in size.

FIELD OF THE INVENTION

The present invention is directed to the field of biotechnology, focusing on developing efficient platforms for expressing proteins in mammalian cells site-specifically incorporating unnatural amino acids.

BACKGROUND OF THE INVENTION

Site-specific incorporation of unnatural amino acids (Uaas) holds much potential to probe and engineer the biology of mammalian cells. Central to this technology is a nonsense-suppressing aminoacyl-tRNA synthetase (aaRS)/tRNA pair, which is engineered to charge the tiaa of interest without cross-reacting with any of its host counterparts. Such "orthogonal" aaRS/tRNA pairs are typically imported into the host cell from a different domain of life. The performance of the heterologous suppressor tRNA is often suboptimal in the new host, given it must directly interact with a nonnative translation system. Indeed, several studies have confirmed that Uaa incorporation efficiency in mammalian cells is limited by the poor performance of the heterologous suppressor tRNAs, which must be massively overexpressed for acceptable efficiency of Uaa incorporation. While such high levels of tRNA expression can be achieved through transient transfection in specific mammalian cell lines that exhibit high transfection efficiency, it is challenging to do so in difficult-to-transfect cells (e.g., primary cells, neurons, stem cells, etc.). Moreover, it makes generation of stable suppressor cell-lines (that express engineered aaRS/tRNA from the genome) very challenging, as hundreds of copies of tRNA gene must be inserted into the genome to reach sufficient nonsense suppression/Uaa incorporation efficiency. The ability to overcome the suboptimal performance of the suppressor tRNA will significantly improve the robustness of the Uaa mutagenesis technology, facilitating advanced applications such as facile generation of stable suppressor cell lines capable of Uaa incorporation and simultaneous incorporation of Uaas at multiple sites in the same protein.

SUMMARY OF THE INVENTION

The origins of poor tRNA performance are often unclear, making it challenging to address the poor performance by rational design. However, improved orthogonal suppressor tRNAs are frequently generated through directed evolution for Uaa incorporation in E. coli; clever selection systems have been developed that enable facile enrichment of active yet orthogonal suppressor tRNA mutants from large synthetic libraries. The ability to perform analogous tRNA evolution in mammalian cells holds enormous potential to create improved suppression systems, but no suitable platform is currently available. It is important to perform such directed evolution experiments in mammalian cells to ensure that the tRNA mutants are selected based on their improved interactions with the unique mammalian translation system.

Existing directed evolution strategies in mammalian cells almost exclusively rely on stable integration of the target gene in a cell line, followed by the creation of sequence diversity through untargeted or targeted random mutagenesis. The associated low mutagenic frequency is not suitable for tRNA evolution, given its small size (<100 bp). Furthermore, to successfully evolve the stem regions of a tRNA, which are the most frequent targets for engineering, any mutation must be accompanied by a matching mutation on the other side to retain base-pairing. Capturing such rich sequence diversity within the small tRNA gene is only feasible using synthetic site-saturation mutant libraries. To enrich suppressor tRNA variants that are orthogonal and active in mammalian cells from such libraries, it is necessary to have: i) controlled delivery of the library, such that each cell receives a single variant; ii) a selection scheme that enriches the active tRNA mutants, and removes cross-reactive ones; and iii) the ability to identify the surviving mutants. No selection system currently exists that meets these criteria.

Described herein are compositions comprising variant/mutant nonsense suppressing tRNA molecules (also referred to herein as suppressor tRNAs) having increased biological activity relative to the corresponding wild type suppressor tRNA molecule to incorporate an unnatural amino acid (Uaa or UAA) into a mammalian protein; expression vectors (e.g., viral vectors) encoding these variant tRNAs where the vectors are suitable for infecting mammalian cells; mammalian cells comprising these expression vectors (e.g., viral vectors); methods of producing suppressor tRNAs with increased biological activity using the virus-assisted directed evolution methods described herein; methods of using these tRNAs with increased activity to produce proteins with site-specifically incorporated unnatural amino acids and kits containing reagents comprising the variant tRNAs and other reagents required for producing such proteins.

In particular, the compositions of the present invention comprise, for example, a variant archaeal or bacterial nonsense suppressing tRNA molecule, wherein the orthogonal, active variant tRNA has increased activity to incorporate various unnatural amino acids (e.g., amino acid analogs) into a mammalian protein relative to its "wild type" counterpart suppressor tRNA. The term "wild type" counterpart tRNA as used herein means a suppressor tRNA molecule that has not been subjected to the virus-assisted directed evolution methods described herein to produce (select and enrich) a population of suppressor tRNA molecules having increased biological activity to incorporate a Uaa into a protein of interest in a site specific manner.

The activity of the variant tRNAs encompassed by the present invention is increased over the wild type tRNA, for example, by about 2.5 to about 200 fold, about 2.5 to about 150 fold, about 2.5 to about 100 fold about 2.5 to about 80 fold, about 2.5 to about 60 fold, about 2.5 to about 40 fold, about 2.5 to about 20 fold, about 2.5 to about 10 fold, about 2.5 to about 5 fold, about 5 to about 200 fold, about 5 to about 150 fold, about 5 to about 100 fold, about 5 to about 80 fold, about 5 to about 60 fold, about 5 to about 40 fold, about 5 to about 20 fold, about 5 to about 10 fold, about 10 to about 200 fold, about 10 to about 150 fold, about 10 to about 100 fold, about 10 to about 80 fold, about 10 to about 60 fold, about 10 to about 40 fold, about 10 to about 20 fold, about 20 to about 200 fold, about 20 to about 150 fold, about 20 to about 100 fold, about 20 to about 80 fold, about 20 to about 60 fold, about 20 to about 40 fold, about 40 to about 200 fold, about 40 to about 150 fold, about 40 to about 100 fold, about 40 to about 80 fold, about 40 to about 60 fold, about 60 to about 200 fold, about 60 to about 150 fold, about 60 to about 100 fold, about 60 to about 80 fold, about 80 to about 200 fold, about 80 to about 150 fold, about 80 to about 100 fold, about 100 to about 200 fold, about 100 to about 150 fold, or about 150 to about 200 fold.

Variant archaeal tRNA molecules are derived, for example, from the Methanosarcinacaea or Desulfitobacterium family, and, in particular, from any of the M. barkeri (Mb), M. alvus (Ma), M. mazei(Mm) or D. hafnisense (Dh) families. Specifically, the claimed invention encompasses a variant tRNA which is a pyrrolysyl tRNA (tRNA$^{Pyl}$) derived from SEQ ID NO: 1 or a nucleic acid sequence with at least about 80%, 85%, 86%, 87%, 88%, 89% 90%, 91%, 92%, 93%, 94%, 95%, 96%, 97%, 98%, or 99% sequence identity with any of the full-length SEQ ID NOS: 2-27 of variant tRNA molecules as shown in Table 1. More specifically, in certain embodiments, the variant tRNA$^{Pyl}$ comprises a sequence selected from the group consisting of: SEQ ID NOS: 2-27, or a nucleic acid sequence with at least 80%, 85%, 86%, 87%, 88%, 89% 90%, 91%, 92%, 93%, 94%, 95%, 96%, 97%, 98%, or 99% sequence identity with the full-length SEQ ID NOS: 2-27. In certain embodiments, the tRNA comprises 1, 2, 3, 4, 5, 6, 7, 8, 9, 10 or more than 10 mutations (e.g., substitutions) relative to any one of SEQ ID NOs: 1-27. The unnatural amino acid suitable for incorporation by the variant archaea-derived tRNAs described herein can be azido-lysine (AzK) (structure 1 of FIG. 18) or Nε-acetyllysine (AcK) (structure 2 of FIG. 18), or any other lysyl analogs such as structures 3-6 as shown in FIG. 18. Additionally, as described herein (see e.g., Example 9, (FIG. 19)) incorporation efficiency of any other Uaa, which uses an engineered pyrrolysyl-tRNA synthetase, can also be enhanced through the use of these engineered tRNA$^{Pyl}$ mutants.

The variant bacterial tRNA molecules of the present invention are derived, for example, from an E. coli tRNA, Specifically, the claimed invention encompasses a variant tRNA which is a leucyl tRNA (tRNA$^{Leu}$) derived from SEQ ID NO: 28, Specifically, in certain embodiments, the variant tRNA$^{Leu}$ comprises any one of SEQ ID NOS: 29-45, or a nucleic acid sequence with at least about 80%, 85%, 86%, 87%, 88%, 89%, 90%, 91%, 92%, 93%, 94%, 95%, 96%, 97%, 98%, or 99% sequence identity with any one of the full-length SEQ ID NOS. 29-45. In certain embodiments, the tRNA$^{Leu}$ comprises 1, 2, 3, 4, 5, 6, 7, 8, 9, 10 or more than 10 mutations (e.g., substitutions) relative to any one of SEQ ID NOs: 28-45. Any suitable unnatural amino acid/analog can be used with the methods described herein for incorporation into a protein of interest. In particular, the unnatural amine) acid suitable for incorporation by the variant bacterial-derived tRNAs described herein can be structures 7-12 shown in FIG. 18, or Uaas that are structurally and functionally similar to the structures 7-12. Additionally, as described herein (see for example FIG. 19), incorporation efficiency of any other Uaa, which uses an engineered E. coli leucyl-tRNA synthetase, can also be enhanced through the use of these engineered tRNA$^{Leu}$ mutants.

Also encompassed by the present invention are expression vectors e.g., viral vectors) comprising a variant archaeal or bacterial suppressor tRNA, wherein the variant tRNA has increased activity to incorporate an unnatural amino acid into a mammalian protein relative to its wild type counterpart tRNA as described herein. Viruses suitable for the present invention includes any virus that either does, or does not, integrate with the mammalian cell genome. Such viruses include adenoviruses, adeno-associated viruses, baculovirus, lentiviruses and retroviruses. More specifically, as described herein, any of the serotypes of adeno-associated virus can be used in the present invention, and particularly adeno-associated virus serotype 2. The expression vectors (e.g., viral vectors) of the present invention can also encode reporter genes such as mCherry, GFP or EGFP or other suitable detector molecules.

Also encompassed by the present invention is a cell, or cells comprising the expression vectors (e.g., viral vectors) described herein, as well as stable cell lines of these cells. In particular embodiments, the cells are mammalian cells, and the stable mammalian cells comprise the genomically integrated (or episomally maintained) engineered tRNAs.

The cells of the present invention can further comprise one, or more, additional expression vectors (e.g., plasmids) encoding genes required for viral replication of the virus vector in the cell. More particularly, the cells of the present invention may comprise expression vectors (e.g., plasmids) encoding all genetic components essential for viral replication, wherein a nonsense codon is inserted into a protein sequence rendering viral replication dependent on the activity of the variant suppressor tRNA.

In one embodiment the essential viral protein can be the VP1 capsid protein (Cap) of a non-enveloped virus, such as adeno-associated virus AAV2 SEQ NO: 46, or an amino acid sequence comprising about 80%, 85%, 86%, 87%, 88%, 89% 90%, 91%, 92%, 93%, 94%, 95%, 96%, 97%, 98%, or 99% sequence identity with SEQ ID NO: 46. Suppressor codons can be inserted into the capsid protein (e.g., TAG-amber; TAA-ochre or TGA-opal) at selected sites (Agnew.Chem.Int.Ed. 2016, 55, 10645; Agnew.Chem.Int.Ed. 2017, 56, 4234). As described herein, the essential viral protein for adeno-associated virus can be Cap with a TAG codon at position 454. Cells can be cultured in the presence of the cognate Uaa RNA Synthetase (UaaRS) and the Uaa. In one embodiment, the UaaRS is e.g., Mb$^{Pyl}$RS and the Uaa is e.g., AzK or AcK. In another embodiment, the variant tRNA is an E. coli leucyl tRNA (tRNA$^{Leu}$), the aaRS is E. coli LeuRS and the Uaa is a leucine analog such as shown in FIG. 18.

Also encompassed by the present invention is a method of virus-assisted directed evolution of suppressor tRNA variants with increased biological activity relative to the wild type suppressor tRNA. Replication of the virus in mammalian cells requires expression of an essential protein dependent on the activity of the tRNA valiant of interest.

The method comprises the steps of encoding a library of suppressor tRNA variants of interest in a virus genome; infecting a population of mammalian host cells with the virus vectors at low multiplicity of infection (MOI) and maintaining the population of cells under conditions suitable for virus replication in the cells, wherein virus replication in mammalian cells requires expression of an essential protein dependent on the activity of the tRNA variant of interest; and harvesting and selectively amplifying the virus progeny encoding active tRNA variants to remove cross-reactive tRNA molecules, whereby orthogonal suppressor tRNA variants with increased biological activity are recovered. The amplified tRNA variants can then be sequenced to determine their nucleic acid sequences and subjected to further evaluation. Next generation sequencing of the virus-encoded tRNA library before and after the selection can be performed to ascertain the enrichment of each possible mutant in the library. This enrichment factor can used as an indicator of tRNA activity, and the most enriched tRNA mutants can be constructed and tested to verify their activities. In certain embodiments, a disclosed method contemplated method results in a 10,000-30,000 of a 20,000-30,000 fold enrichment of a virus encoding an active tRNA over a virus harboring an inactive tRNA.

In a more particular embodiment, as described herein, sequences of the nonsense-suppressing tRNA of interest are randomized to create libraries and encoded in a suitable expression vector (e.g., viral vector). The tRNA variant libraries will comprise inactive tRNA molecules, active and orthogonal tRNA molecules and active but cross-reactive tRNA molecules.

Certain contemplated methods include the use of a population of competent host cells. Such cells are typically, mammalian cells, and more specifically immortalized human cells. The suitable host cells can be infected with the virus vectors at very low to low multiplicity of infection (MOI). In certain embodiments, the MOI is from about 0.1 to about 15, about 0.1 to about 10, about 0.1 to about 5, about 0.1 to about 3, about 0.1 to 1, about 1 to about 15, about 1 to about 10, about 1 to about 5, about 1 to about 3, about 3 to about 15, about 3 to about 10, about 3 to about 5, about 5 to about 1.5, about 5 to about 10, or about 10 to about 15. In certain embodiments, the MOI is between 0.1 and 5. In certain embodiments, the MOI is less than 15, less than 10, less than 5, less than 3, less than 1 or less than 0.1. In certain embodiments, a single viral vector encoding the variant tRNA is all that is required for expression of the essential viral protein and production of viral progeny in the cell. More specifically, each cell receives a single virus-encoded tRNA variant.

The cells are subsequently (typically within a few hours of virus infection) transfected with one or more expression vectors (e.g., plasmids), wherein the expression vectors (e.g., plasmids) comprise all genetic components essential for viral replication, wherein a nonsense codon is inserted into the protein sequence rendering viral replication dependent on the activity of the variant suppressor tRNA. In one embodiment the essential viral protein is Cap (SEQ ID NO: 46) with a TAG codon at position 454. In certain embodiments, the expression vectors (e.g., plasmids) also encode a cognate Uaa RNA Synthetase (UaaRS). For example, wherein the tRNA library is a pyrrolysyl tRNA (tRNA$^{Pyl}$) library, the UaaRS is Mb$^{Pyl}$ RS. At the time of transfection, the Uaa may also be added to the culture medium at an appropriate concentration. In a particular embodiment, the Uaa is AzK. Alternatively, the variant tRNA is a leucyl tRNA (tRNA$^{Leu}$), the aaRS is *E. coli*$^{Leu}$RS and the Uaa is AzK, or any one of structures 7-12 of FIG. 18. Additional expression vectors (e.g., plasmids) encoding genetic components required for viral replication may also be transfected into the host cell as described herein.

In a contemplated method, the infected/transfected cells are maintained (i.e., cultured) in the media containing the Uaa under conditions suitable for expression of the variant tRNA, expression of the essential viral protein and replication of the virus. In certain embodiments, the cells are harvested, and virus progeny are isolated and subjected to further enrichment to remove cross-reactive but active tRNA molecules, and the orthogonal suppressor tRNA variants with increased biological activity are recovered. The enriched tRNA variants can be sequenced to obtain their nucleic acid sequence. Next-generation DNA sequencing of the virus-encoded tRNA library before and after the selection can be performed to measure the abundance of each tRNA mutant and how they change upon selection. The tRNA mutants that undergo the strongest enrichment upon selection are the ones likely to have the highest activity.

In the methods of the present invention, only active and orthogonal tRNA variants permit the incorporation of the Uaa into the essential viral gene protein and viral replication in the cell. However, in certain embodiments, virus comprising active, cross-reactive tRNAs can also replicate, so an additional step to remove the virus population encoding cross-reactive tRNAs and enrich the virus population encoding the desired tRNAs is required. The isolated virus progeny can be enriched for the tRNA variants with increased biological activity. For example, isolated virus progeny can be chemoselectively labeled with a purification handle/tag attached through a photocleavable moiety such as a photocleavable linker. In one embodiment this moiety is a photocleavable DBCO-sulfo-biotin conjugate. The reaction mixture contains virus incorporating the Uaa protein, virus without the Uaa protein, photocleavable biotin label and excess Uaa as a quencher. The biotin-conjugate labeled virus is recovered using streptavidin coated beads and virus eluted from the beads using a suitable wavelength (e.g., 365 nm). Recovered virions comprise suppressor tRNAs of interest with increased biological activity relative to wild type suppressor tRNAs.

The recovered virus can be lysed, tRNAs amplified and then sequenced to obtain their nucleic acid sequences. Alternatively, the recovered virus can be lysed, the tRNAs amplified and cloned as described above using a suitable vector. Colonies may be then selected for sequencing to obtain the nucleic acid sequence of the suppressor tRNAs of interest. Additionally, next-generation DNA sequencing (e.g., Illumina) of the virus-encoded tRNA library before and after the selection can be performed to measure the abundance of each tRNA mutant and how they change upon selection. The tRNA mutants that undergo the strongest enrichment upon selection are the ones likely to have the highest activity. The identified mutants can then be constructed and tested.

Further encompassed by the present invention are methods of producing a protein of interest in a mammalian cell with one, or more, amino acid analogs at specified positions in the protein. In one embodiment, the steps of the method comprises culturing the mammalian cell in a culture medium under conditions suitable for growth, wherein the cell comprises a nucleic acid that encodes a protein with one, or more, selector codons and the cell also comprises a variant archaea-derived pyrrolysyl tRNA with increased biological activity that recognizes the selector codon and its cognate aminoacyl-RNA Synthetase. The cell culture medium may be contacted (added in the appropriate concentration) with one, or more, lysine analogs under conditions suitable for incorporation of the one, or more, lysine analogs into the protein in response to the selector codon, thereby producing the protein of interest (desired protein) with one, or more lysine analogs.

In one embodiment the variant tRNA is a pyrrolysyl tRNA (tRNA$^{Pyl}$) derived from SEQ ID NO: 1, or a nucleic acid sequence with at least 80%, 85%, 86%, 87%, 88%, 89% 90%, 91%, 92%, 93%, 94%, 95%, 96%, 97%, 98%, or 99% sequence identity with any of the full-length SEQ ID NOS: 2-27. In a particular embodiment, the variant tRNA comprises a sequence selected from the group consisting of: SEQ ID NOS: 2-27, or a nucleic acid sequence with at least 80%, 85%, 86%, 87%, 88%, 89% 90%, 91%, 92%, 93%, 94%, 95%, 96%, 97%, 98%, or 99% sequence identity with the full-length SEQ ID NOS: 2-27, The lysine analog can be any lysyl analog, and in particular is either azidolysine (AzK) or acetyllysine (AcK) or any of the structures 3-6 of FIG. 18. Additionally, as described in Example 9 (FIG. 19), incorporation efficiency of any other Uaa, which uses an engineered pyrrolysyl-tRNA synthetase, can also be enhanced through the use of these engineered tRNA$^{Pyl}$ mutants.

In another embodiment of the method, the variant suppressor tRNA is an *E. coli*-derived leucyl tRNA with increased biological activity that recognizes the selector codon, and its cognate amino acyl-RNA synthetase and incorporates one, or more, leucine analogs into the protein of interest in response to the selector codon, thereby producing the protein with one, or more leucine analogs. In one embodiment, the variant tRNA is a leucyl tRNA (tRNA$^{Leu}$) derived from SEQ ID NO: 28. In a particular embodiment, the variant tRNA$^{Leu}$ comprises any one of SEQ D NOs: 29-45 or a nucleic acid sequence with at least 80%, 85%, 86%, 87%, 88%, 89% 90%, 91%, 92%, 93%, 94%, 95%, 96%, 97%, 98%, or 99% sequence identity with any one of the full-length SEQ ID NOs: 29-45. The unnatural amino acid suitable for incorporation by the variant bacterial-derived tRNAs described herein can be structures 7-12 shown in FIG. 18, Additionally, as described in Example 9 (FIG. 19, incorporation efficiency of any other Uaa, which uses an engineered *E. coli* leucyl-tRNA synthetase, can also be enhanced through the use of these engineered tRNA$^{Leu}$ mutants.

The methods of the present invention further encompass a method of site-specifically incorporating one, or more, azido-lysine (AzK) or acetyl-lysine (AcK) residues into a protein or peptide in a cell, the method comprising culturing the cell in a culture medium under conditions suitable for growth, wherein the cell comprises a nucleic acid that encodes a protein or peptide of interest with one, or more, amber, ochre or opal selector codons at specific sites in the protein or peptide, wherein the cell further comprises a variant archaea-derived pyrrolysyl-tRNA$^{Pyl}$ with increased biological activity that recognizes the selector codon, and further comprises an archaeal Pyl-tRNA synthetase. The cell culture medium may then be contacted with one, or more, AzK or AcK residues under conditions suitable for incorporation of the one, or more, AzK or AcK residues into the protein or peptide at the one, or more sites of the selector codon(s), thereby producing the protein or peptide of interest with one, or more site-specifically incorporated AzK or AcK residues.

In one embodiment the variant pyrrolysyl tRNA (tRNA$^{Pyl}$) is derived from SEQ ID NO: 1. For example, the variant tRNA$^{Pyl}$ comprises a sequence selected from the group consisting of: SEQ ID NOS: 2-27, or a nucleic acid sequence with at least 80%, 85%, 86%, 87%, 88%, 89% 90%, 91%, 92%, 93%, 94%, 95%, 96%, 97%, 98%, or 99% sequence identity with anyone of the full-length SEQ ID NOS: 2-27. Also see, for example, FIG. 18, structures 1-6.

In another embodiment the method site-specifically incorporates one, or more, leucine analog residues into a protein or peptide in a cell, wherein the cell comprises a variant *E. coli*-derived tRNA$^{Leu}$ with increased biological activity that recognizes the selector codon, and further comprises an *E. coli* Leu-tRNA synthetase. The cell culture medium may be contacted with one, or more, leucine analog residues under conditions suitable for incorporation of the one, or more, leucine analog residues into the protein or peptide at the sites of the selector codon(s), thereby producing the protein or peptide of interest with one, or more site-specifically incorporated leucine analog residues.

Specifically, in certain embodiments, the variant tRNA is a leucyl tRNA (tRNA$^{Leu}$) derived from SEQ ID NO: 28. For example, the variant tRNA$^{Leu}$ comprises any one of SEQ ID NOS: 29-45, or a nucleic acid sequence with at least 80%, 85%, 86%, 87%, 88%, 89% 90%, 91%, 92%, 93%, 94%, 95%, 96%, 97%, 98%, or 99% sequence identity with any one of the full-length SEQ ID NOs: 29-45. The unnatural amino acid suitable for incorporation by the variant bacterial-derived tRNAs described herein can be structures 7-12 shown in FIG. 18. Additionally, as described in Example 9 (FIG. 19) incorporation efficiency of any other Uaa, which uses an engineered *E. coli* leucyl-tRNA synthetase, can also be enhanced through the use of these engineered tRNA$^{Leu}$ mutants.

Also encompassed by the present invention are kits for producing a protein or peptide of interest in a cell, wherein the protein or peptide comprises one, or more lysine analogs, the kit comprising a container containing a polynucleotide sequence encoding variant archaea-derived tRNA$^{Pyl}$ with increased biological activity that recognizes a selector codon in a nucleic acid of interest in a cell. Specifically, in certain embodiments, the variant tRNA$^{Pyl}$ comprises a sequence selected from the group consisting of: SEQ ID NOS: 2-27 (see for example, FIG. 18, structures 1-6), or a nucleic acid sequence with at least 80%, 85%, 86%, 87%, 88%, 89% 90%, 91%, 92%, 93%, 94%, 95%, 96%, 97%, 98%, or 99% sequence identity with any of the full-length SEQ ID NOS: 2-27. The kit can further comprise a container containing a nucleotide sequence encoding archaea Pyl-tRNA synthetase. The kit can further comprise one, or more, lysine analogs, such as azidolysine (AzK) or acetyllysine (AcK). The kit can also include instructions for producing the protein or peptide of interest.

In an alternative embodiment, the kit is directed to producing a protein or peptide of interest in a cell, wherein the protein or peptide comprises one, or more leucine analogs, the kit comprising a container containing a polynucleotide sequence encoding variant *E. coli* derived tRNA$^{Leu}$ with increased biological activity that recognizes a selector codon in a nucleic acid of interest in a cell, wherein the variant tRNA$^{Leu}$ comprises any one of SEQ ID NOs: 29-45, or a nucleic acid sequence with at least 80%, 85%, 86%, 87%, 88%, 89%, 90%, 91%, 92%, 93%, 94%, 95%, 96%, 97%, 98%, or 99% sequence identity with any one of the full-length SEQ ID NOS: 29-45. The kit can also comprise a container containing a polynucleotide sequence encoding an *E. coli* Leu-tRNA Synthetase and one, or more, leucine analogs, such as structures 7-12 in FIG. 18. The kit can include instructions for producing the protein or peptide of interest.

Also encompassed by the present invention is a mammalian cell with a stably integrated variant tRNA-Pyl or tRNA-Leu for Uaa incorporation. In one embodiment, the mammalian cell comprises a variant tRNA-Pyl-Leu, wherein the sequence of the variant tRNA-Pyl-Leu is selected from the group consisting of SEQ ID NOS: 2-27, and wherein the Uaa is a pyrrolysyl residue selected from the group consisting of any of the structures 1-7. In another embodiment, the cell comprises a variant tRNA-Leu which is selected from the group consisting of SEQ ID NOS: 29-45 and the Uaa, is a leucine analog selected from the group consisting of any of the structures 7-12.

More specifically, encompassed herein is an engineered mammalian cell that comprises less than 250, 200, 150, 100, 75, 50 copies of a gene encoding a variant suppressor tRNA capable of incorporating an unnatural amino acid into a pre-selected protein (for example, a protein expressed from a gene containing a premature stop codon) expressed in the cell. It is contemplated that the cell may comprise 25-250, 25-200, 25-150, 25-100, 25-75, 25-50, 50-250, 50-200, 50-150, 50-100, 50-75, 75-250, 75-200, 75-150, 75-100, 100-250, 100-200, 100-150 copies of the gene encoding the suppressor tRNA. Given the increased efficiency of incorporation of amino acids into a target protein using the variant tRNAs developed using the VADER approach, then fewer tRNAs are required to the introduced into a cell than wild type tRNAs to obtain the desired protein expression level. The fewer number of exogenous tRNAs introduced into the cell is expected to have a less disruptive effect on the structure, function, or viability of the host cell.

The current invention demonstrates features and advantages that will become apparent to one of ordinary skill in the art upon reading the attached Detailed Description.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings:

(FIG. 2a discloses SEQ ID NO: 1) b, Analysis of tRNA sequences emerging from the selection of each library. c, Efficiency of TAG suppression for each of the unique fully base-paired tRNA$^{Pyl}$ selectants measured using an EGFP-39TAG reporter. The tRNA encoded in the pAAV plasmid (also harboring a wild-type mCherry reporter) was cotransfected into HEK293T cells with MbPylRS and EGFP-39TAG in the presence or absence of 1 mM AzK. Expression of EGFP-39TAG facilitated by each tRNA$^{Pyl}$ mutant was measured in cell-free extract, normalized relative to wild-type mCherry expression and plotted as a percentage of the reporter expression facilitated by wild-type tRNA$^{Pyl}$. Data shown as mean±s.d. (n=3 independent experiments).

FIG. 4a-b shows that single AAV2-encoded tRNA gene can facilitate the expression of TAG-inactivated capsid gene (Cap) and the production of progeny virus. a, Scheme of the experiment. HEK293T cells are infected with AAV2 encoding a tRNACUA$^{Pyl}$ and a wild-type EGFP gene at a very low MOI, then further transfected with plasmids encoding: i) AAV2 Rep and Cap-454-TAG genes, ii) MbPylRS, and iii) AdHelper in the presence or absence of 1 mM AzK. The feasibility of packaging AAV2 incorporating AzK at the 454 position of Cap, and that it does not perturb the virus, have been previously demonstrated Suppression of the TAG codon at 454 position of Cap leads to AzK incorporation into all three overlapping capsid proteins, VP1, VP2 and VP3 (60 total copies), at a surface exposed site. An identical experiment in which Cap-454-TAG is replaced by a wild-type Cap, was also performed. After 48 hours, the progeny virus was harvested from these cells and titered by infecting freshly seeded HEK293T cells, followed by their FACS analysis. b, AzK-dependent production of progeny virus is observed when Cap-454-TAG is used (magnified in the inset); the efficiency is significantly lower than the identical experiment where wild-type Cap is used instead. Data shown as mean±s.d. (n=3 independent experiments).

FIG. 5a-c shows AAV2-454-AzK can be isolated by bioorthogonal attachment of a photo-cleavable DBCO-biotin conjugate followed by streptavidin binding and photo-release. a, Structure of the photocleavable DBCO-biotin conjugate. b, AM/2-454-AzK was treated with different concentrations of the DBCO-biotin for 1 hr, the reaction was quenched using excess AzK, and the small molecules were removed by dialysis. The biotin-labeled virus was captured using streptavidin-agarose, then released by 365 rim irradiation. The infective titer of the virus was measured (by infecting HEK293T cells followed by FACS) before treatment, after biotin modification, and after photo-release, then normalized for volume change. Infectivity relative to untreated virus was plotted. We find that a low degree of biotinylation (at 5 µM reagent; each virion harbors 60 AzK residues) does not affect the AAV2 infectivity, but increased modification of the capsid (at higher DBCO-biotin concentrations) does. Also, using 5 µM DBCO-biotin, modified virus is recovered from streptavidin resin with good efficiency (~30%), whereas the yield is poor when higher reagent concentration is used. c, Using this optimized labeling/capture strategy, AAV2-454-AzK encoding an mCherry reporter can be enriched from its mixture with an EGFP-encoding AAV2 with wild-type capsid (no azide). Fluorescence microscopy images of HEK293T cells infected with the mixed virus population before and after the selection are shown.

FIG. 9 shows sequences of selected tRNAs that are fully base-paired (including G-2U wobble pairing) from each of the four libraries. See FIG. 2*c* for the characterization of their activity. The numbering scheme for the tRNA is shown below.

FIG. 18 shows structures of Uaas used in the methods described herein.

FIG. 20 shows the amino acid sequence (SEQ ID NO: 46) of the AAV2 VPI capsid protein.

DETAILED DESCRIPTION OF THE PREFERRED EMBODIMENTS

Figure 1:
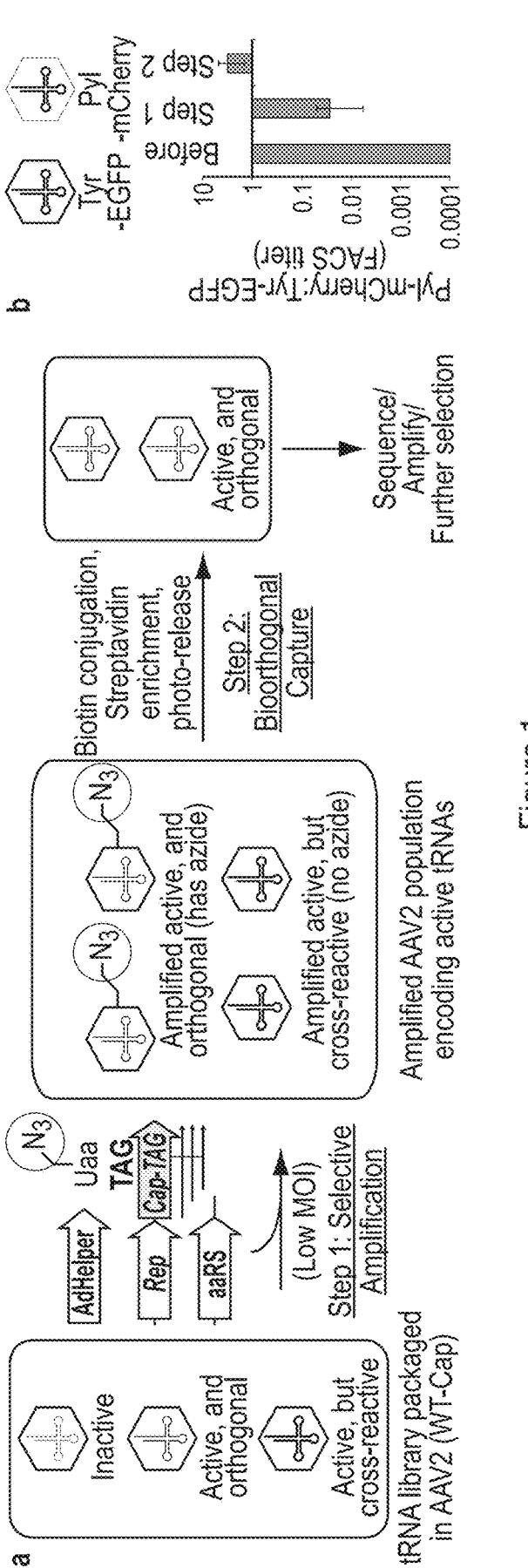
FIG. 1a-b shows the VADER selection scheme. a, Mammalian cells are infected with AAV2 encoding the tRNA library at low MOI. Plasmids encoding TAG-mutant of Cap, other genetic components needed for AAV replication, and the cognate aaRS are provided in trans by transfection in the presence of a suitable azido-Uaa. Active and orthogonal tRNA mutants facilitate generation of packaged progeny AAV2 incorporating the Uaa into their capsid, which are isolated by chemoselective biotin conjugation followed by streptavidin pulldown. b, Two AAV2 vectors, encoding i) *E. coli* tRNA$^{Tyr}$ and EGFP (Tyr-EGFP), and ii) tRNA$^{Pyl}$ and mCherry (Pyl-mCherry), were mixed in $10^4$:1 ratio and subjected to the VADER selection scheme using MbPylRS and its substrate AzK. FACS analysis of the surviving population show >30,000 fold cumulative enrichment of PylmCherry. Data shown as mean±s.d. (n=3 independent experiments).
Figure 2:
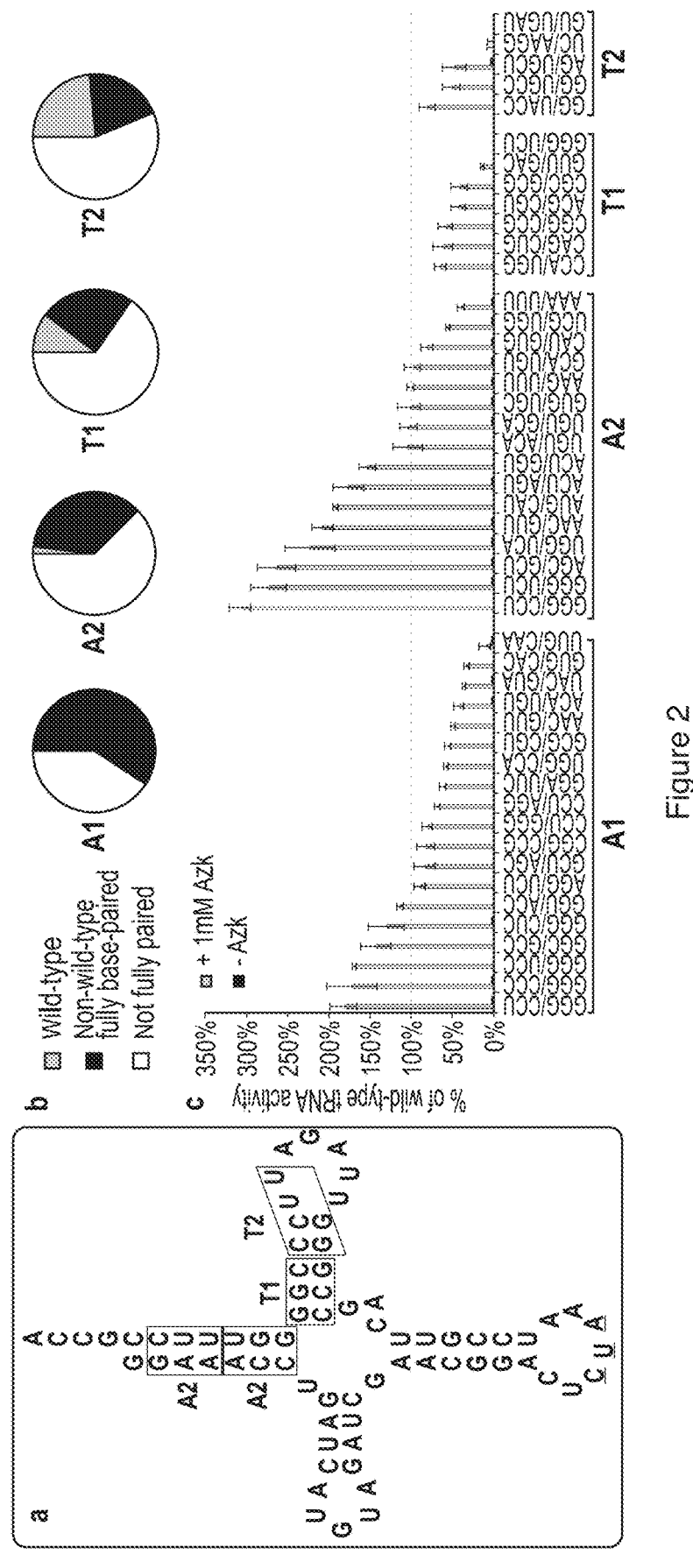
FIG. 2a-b shows Directed evolution of tRNACUA$^{Pyl}$. a, The sequences randomized to create four different libraries (A1, A2, T1, T2) of tRNACUA$^{Pyl}$ are highlighted in four different colors.
Figure 3:
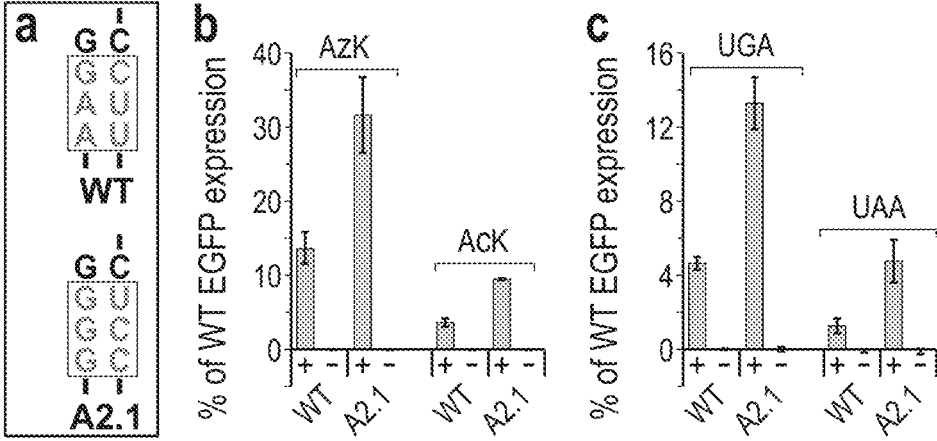
FIG. 3a-c shows improved efficiency of A2.1 tRNACUA$^{Pyl}$. a, Sequences of wildtype (WT) and A2.1. b, Expression of EGFP-39TAG using the WT or A2.1 tRNA, with WT or AcK-selective MbPylRS, in the presence (+) and absence (−) of the appropriate Uaa. c, Expression of EGFP-39TGA and EGFP-39TAA using tRNAUCA$^{Pyl}$ and tRNAUUA$^{Pyl}$ (for both WT and A2.1 mutant), respectively, and MbPylRS in the presence or absence of AzK. Expression of EGFP-39TAG is measured in HEK293T cell-free extract and reported relative to its wild-type counterpart. Data shown as mean±s.d. (n=3 independent experiments).
Figure 6:
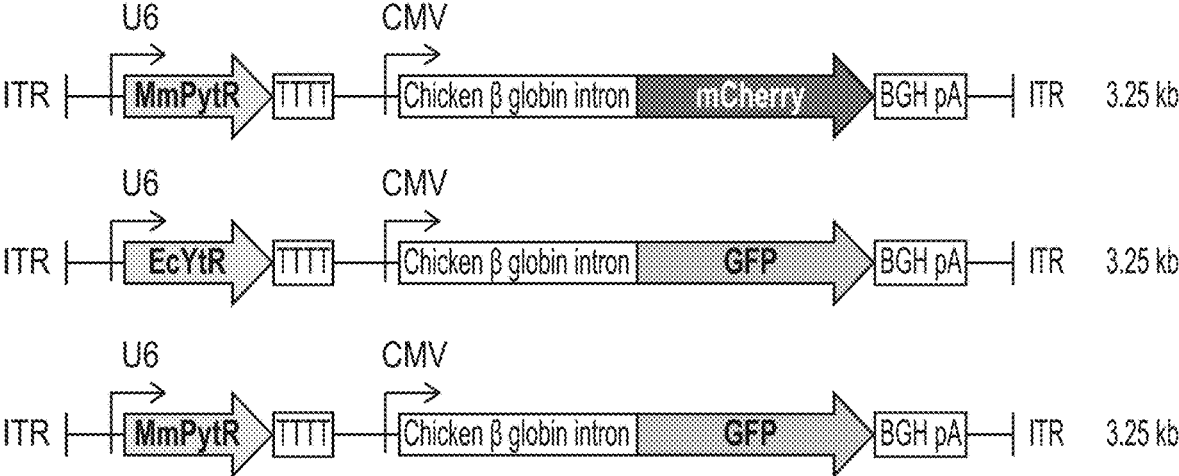
FIG. 6 shows Schematic maps of AAV2 cargoes containing various tRNAs and fluorescent proteins used in this study.
Figure 7:
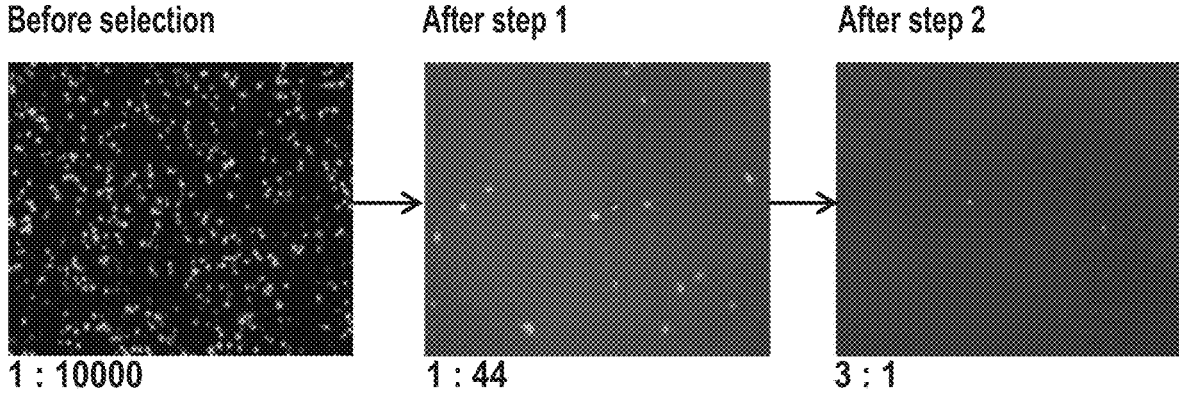
FIG. 7 shows representative microscopy images of cells infected with the mixed. virus population (Tyr-EGFP:Pyl-mCherry) before selection, after step 1, and step 2. Merged images from the EGFP and mCherry channels are shown for each. The ratios of the two viruses (Pyl-mCherry:Tyr-EGFP) as measured by FACS for these experiments are shown below.
Figure 8:
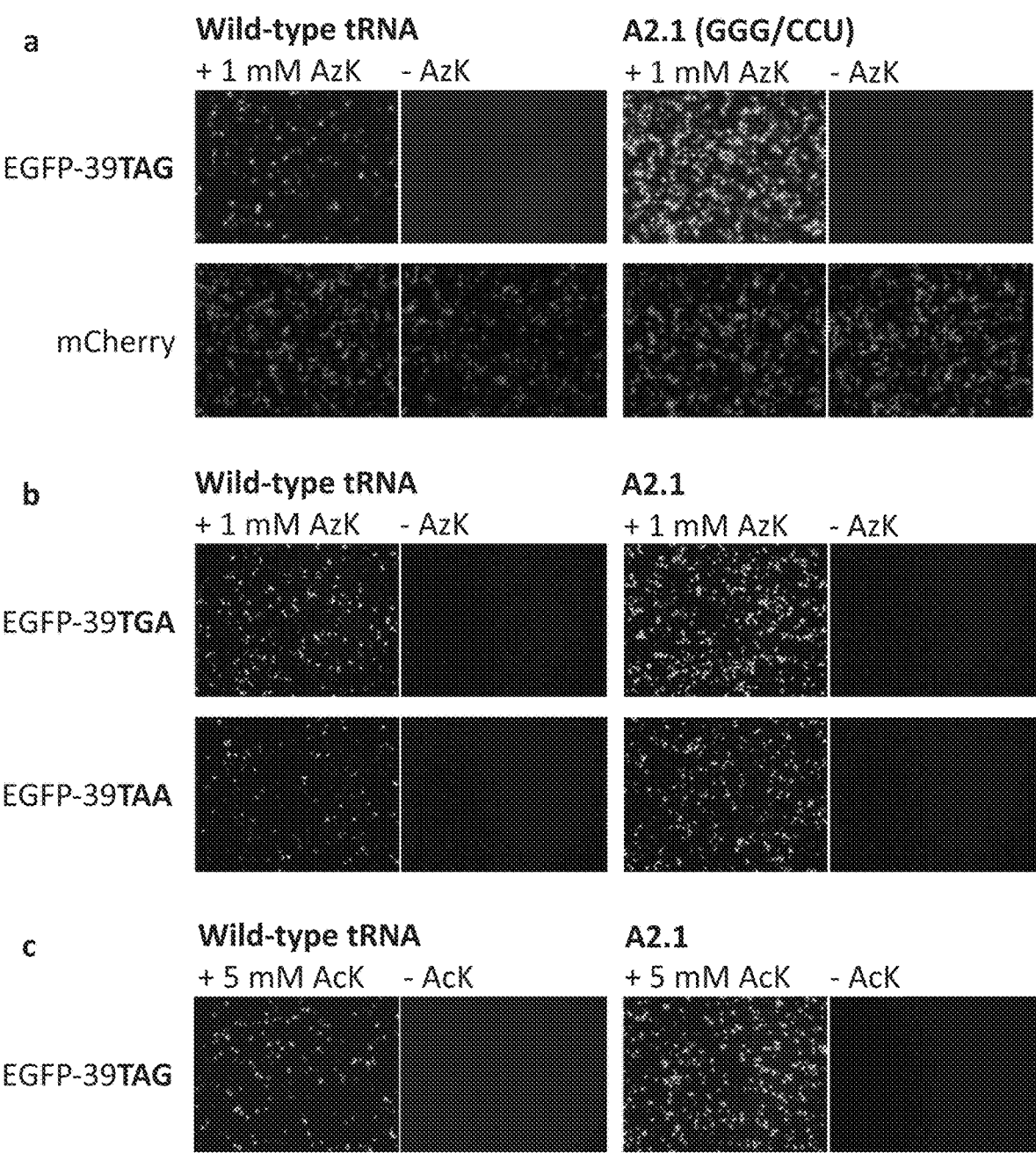
FIG. 8*a-c* shows representative fluorescence microscopy images of HEK293T cells expressing nonsense-inactivated EGFP reporters, suppressed using the wild-type tRNA$^{Pyl}$ or its most efficient evolved mutant, A2.1. a, Co-transfection of wild-type or A2.1 tRNA$^{Pyl}$, encoded in the pAAV plasmid (also encoding a wild-type mCherry reporter) with MbPylRS and EGFP-39-TAG reporter in the presence or absence of 1 mM AzK. Expression of mCherry is shown as a control in each experiment. b, Expression of EGFP-39TGA and EGFP-39TAA using tRNAUCAPyl and tRNAUUA$^{Pyl}$ (for wild-type and A2.1 mutant), respectively. The tRNAs encoded in the pIDTsmart vector were co-transfected with the appropriate EGFP mutant and MbPylRS in the presence or absence of 1 mM AzK. c, Incorporation of AcK into EGFP-39TAG using wild-type and A2.1 tRNA$_{CUA}^{Pyl}$. The tRNAs encoded in the pIDTsmart vector was co-transfected with EGFP-39TAG mutant and MbPylRS-AcKRS3 mutant, in the presence or absence of 5 mM AcK.
Figure 10:
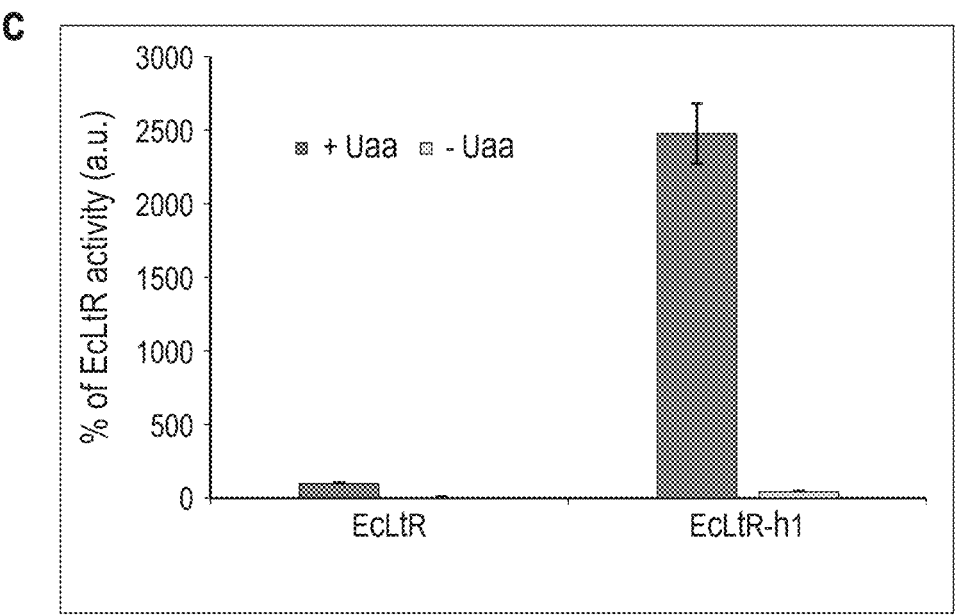
FIG. 10*a-c* shows the improved activity of a mutant leucyl tRNA obtained through the VADER selection scheme. a, shows the sequence of wild-type TAG-suppressor *E. coli* leucyl tRNA (EcLtR) (SEQ ID NO: 47-which is identical to SEQ ID NO:28 but with T not U), b, shows the sequence of one of the improved mutants of EcLtR (EcLtRh1) (SEQ ID NO: 48-identical to SEQ ID NO:30 but with T not U) identified by the methods described herein, c, shows the activity of EcLtR and EcLtR-h1 in HEK293T cells, when co-transfected with an engineered EcLeuRS mutant that selectively charges Uaas. Expression of a fill-length EGFP-39-TAG reporter used to measure the activity of the tRNAs. EcLtR-h1 shows remarkably high efficiency.

The present invention describes a novel strategy, virus-assisted directed evolution of tRNA (VADER) in mammalian cells, to obtain highly efficient active, orthogonal tRNA variant molecules. The tRNA variants as described herein, produced by the methods described herein, are characterized by increased (enhanced) biological activity of nonsense codon suppression and incorporation of unnatural amino acids in a site-specific manner in proteins of interest. The methods to select for these highly efficient tRNA variants couple the activity of the suppressor tRNA to the replication of a human virus (e.g., Adeno-associated virus, or AAV). In certain embodiments, the method comprises: i) encoding the library of tRNA variants in the virus genome to enable its controlled delivery to mammalian cells; ii) inserting a nonsense codon in an essential virus protein to render viral replication dependent on the activity of the suppressor tRNA, facilitating selective amplification of virions encoding active tRNA variants; and iii) the enriched tRNA sequences can be readily retrieved by isolating and sequencing the genome of the freshly amplified virus.

The methods of the present invention specifically demonstrate the ability to enrich an AAV population encoding an active suppressor tRNA relative to AAV population encoding an inactive tRNA in the range of about 10,000 to 50,000-fold and is typically about >30,000 fold, thus providing a powerful selection scheme to enrich active mutants from a naïve tRNA library. In particular, there is a 2.5-fold to 80-fold increase in activity in the variant tRNAs identified and isolated by the methods described herein.

Next generation sequencing (such techniques are known to those of skill in the art-see for example, the kits/reagents commercially available from Illumina) of the virus-encoded tRNA library before and after the VADER selection method described herein can be performed to evaluate and confirm enrichment of each possible mutant/variant in the library.

The technology of the present invention can be further applied to evolve different suppressor tRNAs commonly used for Uaa incorporation in mammalian cells, including, for example, the archaea-derived pyrrolysyl tRNA, and the *E. coli* derived leucyl tRNA, Subjecting synthetic mutant libraries of both tRNAs resulted in the identification of variants that demonstrate significantly improved activity for Uaa incorporation in mammalian cells. The mutants show particularly improved efficiency relative to their wild-type counterparts when expressed at a lower level, further confirming their enhanced intrinsic efficiency.

As a result of the present invention, a general strategy to evolve the efficiency of any engineered suppressor tRNA for Uaa incorporation in mammalian cells is now available. Encoding the tRNA library in a viral genome and subjecting the resulting library to the VADER selection scheme will enable selective enrichment of those that encode active tRNA mutants.

As a result of the present invention, methods are now available that can also be used to evolve the efficiency of other biological parts in mammalian cells, if its activity can be coupled to the expression of AAV capsid proteins. Such biological parts include, but are not limited to, promoter elements, internal ribosomal entry sites (IRES), novel transcription factors, receptor proteins (e.g., GPCR), gene or mRNA editing proteins (e.g., Cas/CRISPR), mammalian two-hybrid systems, etc.

The mutant suppressor tRNAs (e.g., pyrrolysyl and leucyl) generated through the VADER selection scheme as described herein enable highly efficient Uaa incorporation in mammalian cells. These tRNA mutants can be used to improve the yields of Uaa-incorporated protein in mammalian cells (e.g., antibodies and other therapeutically related proteins).

The improved suppressor tRNAs (e.g., pyrrolysyl and leucyl) generated through the VADER selection scheme can be used to create improved expression vectors (e.g., viral vectors) that deliver the genetic machinery for Uaa incorporation into mammalian cells and tissues. Importantly, as these tRNAs are more efficient, fewer copies of tRNA variant need be encoded per genome. Currently, including multiple tRNA copies (to achieve high enough expression of tRNAs) often leads to genome instability of expression vectors (e.g., viral vectors).

The improved suppressor tRNAs (e.g., pyrrolysyl and leucyl) generated through the VADER selection scheme can be used to create stable cell lines for protein expression incorporating Uaas. Currently, the requirement of encoding a large number of tRNA copies per genome makes it challenging to encode the UNA-incorporation machinery stably in the mammalian genome. The increased efficiency of new tRNAs will allow the use of much fewer copies.

The present invention establishes a unique virus-assisted directed evolution platform in mammalian cells capable of improving the activity of tRNAs and other biological parts for biotechnology applications. It also describes suppressor tRNA variants that demonstrate significantly improved activity in mammalian cells.

While this invention has been particularly shown and described with references to preferred embodiments thereof, it will be understood by those skilled in the art that various changes in form and details may be made therein without departing from the scope of the invention encompassed by the appended claims.

Without further elaboration, it is believed that one skilled in the art can, based on the above description, utilize the present invention to its fullest extent. The following specific embodiments and examples are, therefore, to be construed as merely illustrative, and not limitative of the remainder of the disclosure in any way whatsoever.

EXAMPLES

The following examples are provided to illustrate embodiments of the present invention but are by no means intended to limit its scope.

The examples described herein will be understood by one of ordinary skill in the art as exemplary protocols. One of ordinary skill in the art will be able to modify the below procedures appropriately and as necessary.

Materials and Methods

Cell culture. HEK293T cells (ATCC) were maintained at 37° C. and 5% $CO_2$ in DMEM-high glucose (HyClone)

supplemented with penicillin/streptomycin (HyClone, final concentration of 100 U/mL penicillin and 100 μg/mL streptomycin) and 10% fetal bovine serum (Corning). All references to DMEM below refer to the complete medium described here.

General cloning. For all cloning, the *E. coli* TOP10 strain was used for transformation and plasmid propagation and bacteria were grown using LB for solid and liquid culture. All PCR reactions were carried out using Phusion Hot Start II DNA Polymerase (Thermo Scientific) according to the manufacturer's protocol. Restriction enzymes and T4 DNA ligase were from New England Biolabs (NEB). All DNA oligos were purchased from Integrated DNA Technologies (IDT). Sanger sequencing was performed by Eton Bioscience.

Unnatural amino acids Azido-lysine (AzK) was purchased from Iris Biotech GMBH (Germany). Nε-acetyllysine (AcK) was purchased from Bachem.

Packaging and titration of mock and library tRNAs into AAV (wild-type capsid). To package various cargo into AAV-2, 8 million HEK293T cells were seeded in a 10 cm tissue culture dish. The following day, the cells were transfected with 8 μg each of the appropriate cargo plasmid (pAAV-ITR-tRNA-fluorescent protein), pHelper, and pAAV-RC2 using polyethylenimine (PEI) (Sigma). Media was exchanged for fresh DMEM 24 hours after transfection. 72 hours after transfection, the cells were resuspended, pelleted, and lysed by freeze/thawing as previously described. 1 Virus was concentrated and semi-purified by PEG precipitation, 1 resuspended in 1 mL DMEM with FBS and flash frozen.

Sequences Described in the Examples

Wild type and derived sequences described in the Examples and throughout the application are listed in the Table:

| tRNA-Pyl WT | SEQ ID 1 | gGAAACCugaucauguagaucgaacggacucuaaauccguucagccgggguuagauucccggGGUUUCcgcca |
| Pyl hits | SEQ. ID 2 | gGGCGGCugaucauguagaucgaacggacucuaaauccguucagecgggguuagauucccggGCUGCCcgcca |
| | SEQ ID 3 | gGGUGACugaucauguagaucgaacggacucuaaauccguucagecgggguuagauucccggGUUGCCcgcca |
| | SEQ ID 4 | gGGGGGCugaucauguagaucgaacggacucuaaauccguucagccgggguuagauucccggGCUCCCcgcca |
| | SEQ ID 5 | gGGCGGCugaucauguagaucgaacggacucuaaauccguucagccgggguuagauucccggGUUGCCcgcca |
| | SEQ ID 6 | gGGCGCCugaucauguagaucgaacggacucuaaauccguucagccgggguuagauucccggGGCGCCcgcca |
| | SEQ ID 7 | gGGGAGGugaucauguagaucgaacggacucuaaauccguucagccgggguuagauucccggCCUCCCcgcca |
| | SEQ ID 8 | gGGGACCugaucauguagaucgaacggacucuaaauccguucagccgggguuagauucccggGGUCCCcgcca |
| | SEQ ID 9 | gGCCGGGugaucauguagaucgaacggacucuaaauccguucagccgggguuagauucccggCCUGGCcgcca |
| | SEQ ID 10 | gGGGACCugaucauguagaucgaacggacucuaaauccguucagccgggguuagauucccggGGUCCUcgcca |
| | SEQ ID 11 | gGGGCCCugaucauguagaucgaacggacucuaaauccguucagecgggguuagauucccggGGGUCCcgcca |
| | SEQ ID 12 | gGGGGCCugaucauguagaucgaacggacucuaaauccguucagccgggguuagauucccggGGCUCCcgcca |
| | SEQ ID 13 | gGGGUCCugaucauguagaucgaacggacucuaaauccguucagccgggguuagauucceggGGAUCCcgcca |
| | SEQ ID 14 | gGGGACCugaucauguagaucgaacggacucuaaauccguucagccgggguuagauucccggGGUUCCcgcca |
| | SEQ ID 15 | gGGGAGGugaucauguagaucgaacggacucuaaauccguucagccgggguuagauucccggUCUUCCcgcca |
| | SEQ ID 16 | gGGGGGGugaucauguagaucgaacggacucuaaauccguucagccgggguuagauucccggCCCCCUcgcca |
| | SEQ ID 17 | gGUGGGGugaucauguagaucgaacggacucuaaauccguucagccgggguuagauucccggCCCUACcgcca |
| | SEQ ID 18 | gGGGGUCugaucauguagaucgaacggacucuaaauccguucagccgggguuagauucccggGACUCCcgcca |
| | SEQ ID 19 | gGGUCCCugaucauguagaucgaacggacucuaaauccguucagecgggguuagauucccggGGGGUCcgcca |
| | SEQ ID 20 | gGGGACCugaucauguagaucgaacggacucuaaauccguucagccgggguuagauucccggGGUUCUcgcca |
| | SEQ ID 21 | gGGCGGCugaucauguagaucgaacggacucuaaauccguucagccgggguuagauucccggGCCGCCcgcca |
| | SEQ ID 22 | gAGCACCugaucauguagaucgaacggacucuaaauccguucagccgggguuagauucccggGGUGCUcgcca |
| | SEQ ID 23 | gGGGGGGugaucauguagaucgaacggacucuaaauccguucagccgggguuagauucccggCCCCCCcgcca |
| | SEQ ID 24 | gAGGGGGugaucauguagaucgaacggacucuaaauccguucagccgggguuagauucccggCCCCCUcgcca |
| | SEQ ID 25 | gGGGAGCugaucauguagaucgaacggacucuaaauccguucagccgggguuagauucccggGGUUCCcgcca |
| | SEQ ID 26 | gGGGAGCCugaucauguagaucgaacggacucuaaauccguucagccgggguuagauucccggGGUUCCcgcca |
| | SEQ ID 27 | gAGGACCugaucauguagaucgaacggacucuaaauccguucagccgggguuagauucccggGGUUCUcgcca |
| LeuWT | SEQ ID 28 | GCCCGGAugguggaaucgguagacacaagggauucuaaaucccucggcguucgcgcugugcgggguucaaguccgcUCCGGGUacca |

-continued

```
Leu hits   SEQ    GCCCGGAuggguggaaucgguagacacaaggggauucuaaaucccucggcguucgcgcugugcggguuc
           ID 29  aagucccgcUCCGGGCacca
           SEQ    GCCCGGAuggguggaaucgguagacacaagggaCucuaaaucccucggcguucgcgcugugcggguuc
           ID 30  aagucccgcUCCGGGCacca
           SEQ    GGGCGUGuggguggaaucgguagacacaagggauucuaaaucccucggcguucgcgcugugcggguuc
           ID 31  aagucccgcCGCGCCCacca
           SEQ    GGGCGCGuggguggaaucgguagacacaagggauucuaaaucccucggcguucgcgcugugcggguuc
           ID 32  aagucccgcCGCGCCCacca
           SEQ    GGGCAUGuggguggaaucgguagacacaagggauucuaaaucccucggcguucgcgcugugcggguuc
           ID 33  aagucccgcCAUGCCCacca
           SEQ    GGGCACGuggguggaaucgguagacacaagggauucuaaaucccucggcguucgcgcugugcggguuc
           ID 34  aagucccgcCGUGCCCacca
           SEQ    GGGGGUGuggguggaaucgguagacacaagggauucuaaaucccucggcguucgcgcugugcggguu
           ID 35  caagucccgcCGCCCCCacca
           SEQ    GGGGGCGuggguggaaucgguagacacaagggauucuaaaucccucggcguucgcgcugugcggguuc
           ID 36  aagucccgcCGUGCCCacca
           SEQ    GGGGAUGuggguggaaucgguagacacaagggauucuaaaucccucggcguucgcgcugugcggguu
           ID 37  caaguccegcCGUCCCCacca
           SEQ    GGGGACGuggguggaaucgguagacacaagggauucuaaaucccucggcguucgcgcugugcggguuc
           ID 38  aagucccgcCGUGCCCacca
           SEQ    GCCCGUAuggguggaaucgguagacacaagggauucuaaaucccucggcguucgcgcugugcggguuc
           ID 39  aagucccgcUGCGGGCacca
           SEQ    GGGAUAGuggguggaaucgguagacacaagggauucuaaaucccucggcguucgcgcugugcggguuc
           ID 40  aagucccgcCUAUCCCacca
           SEQ    GGGCAUGuggguggaaucgguagacacaagggauucuaaaucccucggcguucgcgcugugcggguuc
           ID 41  aagucccgcCGUGCCCacca
           SEQ    GGGCAGAuggguggaaucgguagacacaagggauucuaaaucccucggcguucgcgcugugcggguuc
           ID 42  aagucccgcUCUGCCCacca
           SEQ    GGGCGUAuggguggaaucgguagacacaagggauucuaaaucccucggcguucgcgcugugcggguuc
           ID 43  aagucccgcUGCGCCCacca
           SEQ    GGGCAAGuggguggaaucgguagacacaagggauucuaaaucccucggcguucgcgcugugcggguuc
           ID 44  aagucccgcCGUGCCCacca
           SEQ    GCACACAuggguggaaucgguagacacaagggauucuaaaucccucggcguucgcgcugugcggguuc
           ID 45  aagucccgcUGUGUGCacca
```

Example 1: Positive Selection 8 million HEK293T cells each were seeded in three 10 cm tissue culture dishes. The next day, the cells were infected with virus containing a tRNAPyl library at an apparent MOI of 5 (the actual MOI is substantially reduced in the presence of PEI, the transfection reagent). Four hours after infection, the cells were transfected with 22 μg of pHelper and 10 μg of pIDTSmart-RC2(T454TAG)-PylRS per dish using PEI. 1 mM AzK was also added at this point. One day after transfection the culture media was exchanged with fresh DMEM containing 1 mM AzK. Cells were harvested three days after transfection and lysed as for virus isolation. The culture media was saved and recombined with clarified lysate, and this mixture was treated with 500 U universal nuclease (Thermo Scientific) for 30 minutes. Virus was recovered by PEG precipitation using 11% polyethylene glycol (Fisher) as previously described 1 and resuspended in 3 mL PBS. The small-scale mock positive selections were carried out in 12-well plates. 0.7 million cells per well were seeded and infected the next day with AAV carrying a tRNAPyl-mCherry cargo. Four hours later the cells were transfected as described for the above selections, but with the transfection mix and AzK scaled down by a factor of 15. For PEI only wells, cells received a comparable amount of transfection reagent but no plasmid. Media was changed the day after transfection for fresh DMEM containing 1 mM AzK. Virus was harvested three days post-transfection and PEG-precipitated as described for the selections above. Confluent cells in a 12-well plate were infected with the entire output of one mock selection well and analyzed by flow cytometry.

Example 2: Negative Selection

The virus from positive selection (3 mL) was labeled with photocleavable DBCO-sulfo-biotin (Jena Biosciences) at a concentration of 5 μM for one hour in the dark with mixing. Immediately after labeling, excess DBCO-biotin was quenched with AzK (1 mM final concentration) and the reactions were dialyzed overnight using Slide-A-Lyzer 100 kDa MWCO devices (Thermo Scientific) against 1 L PBS at 4° C. The dialyzed virus mixtures were split into three 2 mL tubes and each rotated overnight with 400 μL streptavidin agarose resin (Thermo Scientific) at 4° C. The next day, each tube of beads was washed eight times with 1 mL PBS containing additional NaCl (final concentration 300 mM) with mixing between washes. Finally, the washed beads were resuspended in 8 mL PBS (300 mM NaCl) and the virus was eluted from the resin via four 30-second irradiations using a 365 nm UV diode array (Larson Electronics), with mixing between irradiations.

Example 3: Viral DNA Recovery, Amplification, and Cloning

The eluted virus was concentrated from 3 mL to 300 μL using Amicon Ultra-4 100 kDa MWCO centrifugal concentrators (Millipore). This mixture was heated to 100° C. for 10 minutes in order to denature the viral capsid proteins and expose the DNA. Viral DNA was then cleaned up and concentrated by ethanol precipitation using yeast tRNA (Ambion) and resuspended in a final volume of 50 μL. 20 μL of this mixture was added to a 200 μL PCR reaction and amplified with tRNAAmp-F and R primers. The resulting DNA was digested with KpnI and NcoI and cloned into the library cloning vector using the same protocol as for original library generation.

Example 4: Mock Selections Using Pyl-mCherry
and Tyr-GFP

The mock selections shown in FIG. 1 followed the same protocol as above, except that the starting library virus was a 1:10,000 mixture of virus made from pAAV-ITR-PytR-mCherry to virus made from pAAV-ITR-EcYtR-GFP. Mock selection results were analyzed by flow cytometry as described for virus titering, but here cells in a 12-well plate were infected with 200 μL of the virus pool after either positive or negative selection. Red and green fluorescent cells were counted to determine the virus ratio.

Example 5: Hit Sequencing and Characterization

For each library, 30-50 colonies were picked from the transformation plates generated above and sent for Sanger sequencing (Eton Bioscience). All sequences in which all randomized bases were paired were treated as potential hits, and these tRNAs were subcloned into pAAV-ITR-PytR-mCherry for analysis. Initial hit analysis was conducted by transfecting HEK293T cells in 24-well plates with 0.5 μg each of a potential hit pAAV-ITR-PytR-mCherry plasmid, pIDTSmart-MbPylRS, and pAcBacl-GFP(39TAG) in the presence and absence of 1 mM AzK. Two days after transfection, cells were lysed with CelLytic M buffer (Sigma) and EGFP and mCherry fluorescence were measured on aMolecular Devices SpectraMax M5 microplate reader. Values for an untransfected well were subtracted, and EGFP-fluorescence was normalized to mCherry fluorescence for each well. The best hit, Ac2.1 (GGG/CCU), was selected for further analysis with other stop codons and a different synthetase and Uaa, AcKRS3 and AcK. HEK293T cells in a 12-well plate were transfected with 0.375 μg pIDTSmart-PytR containing either the wild-type or evolved tRNA, 0.375 μg pIDTSmartaaRS containing the appropriate synthetase, and 0.75 μg pAcBacl-EGFP containing one or two of the appropriate stop codons. A wild-type EGFP control well used pIDTSmart-PytR(TAG, wild-type), pIDTSmart-MbPylRS, and pAcBacl-EGFP(wild-type) in the same ratios. Two days after transfection, cells were lysed and EGFP fluorescence was measured by microplate reader. Values from an untransfected well were subtracted.

Example 6: Further Evolution of the
Pyrrolysyl-tRNA Using Custom-Randomized
Mutant Libraries In the first-generation VADER experiments, only short segments of the tRNA (3 base pairs at one time) were randomized at one time to create small mutant libraries, which were subjected to selection. While it led to the identification of improved mutants, we surmised that the ability to randomize and select a larger sequence space may lead to the identification of even more efficient mutants. However, randomizing a larger segment of the tRNA exponentially increases the size of the library. For example, randomizing one additional base pair in the stem region increases the number of library members by 16 fold. Because of technical limitations, it is currently challenging to use our VADER platform to process a library size larger than $10^5$, while ensuring complete coverage of all possible mutants. This size limit restricts us to the complete randomization of no more than 4 base pairs in the stem region of a tRNA for engineering its activity. However, when a base pair in a tRNA-stem region is completely randomized, only 6 out of the 16 resulting mutants can still maintain the base pairing interaction (either A:T, G:C, or G:U), which is essential for the stability of the stem region. The majority of mutants that cannot base pair result in an unpaired 'bubble' in the middle of the tRNA stem, which typically compromises tRNA performance. A different way of synthesizing the tRNA library was envisioned, where each base pair is only randomized to the desirable base-paired sequences. This approach takes advantage of the recent advances in DNA synthesis technology, enabling the synthesis of a large number of distinct DNA oligonucleotides of significant length (up to 300 nucleotides). This enables the synthesis of a DNA library, encoding the entirety of the tRNA gene, where each position of each library member can be specified, making it possible to only include mutants that base pair and avoid those which do not.

Figure 11:
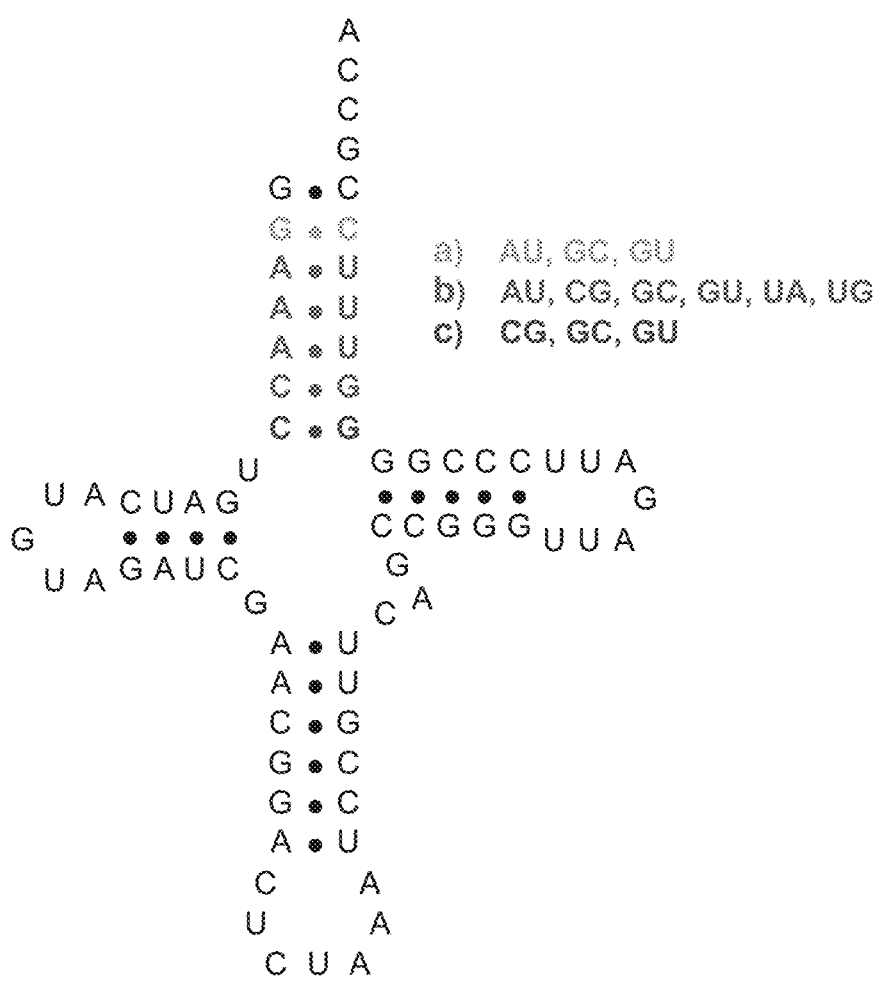
FIG. 11 shows the sequence and the secondary structure of the wild-type pyrrolysyl tRNA (SEQ ID NO:1), and further shows the custom randomization targeted to each position in the acceptor stem to produce.
Figure 12:
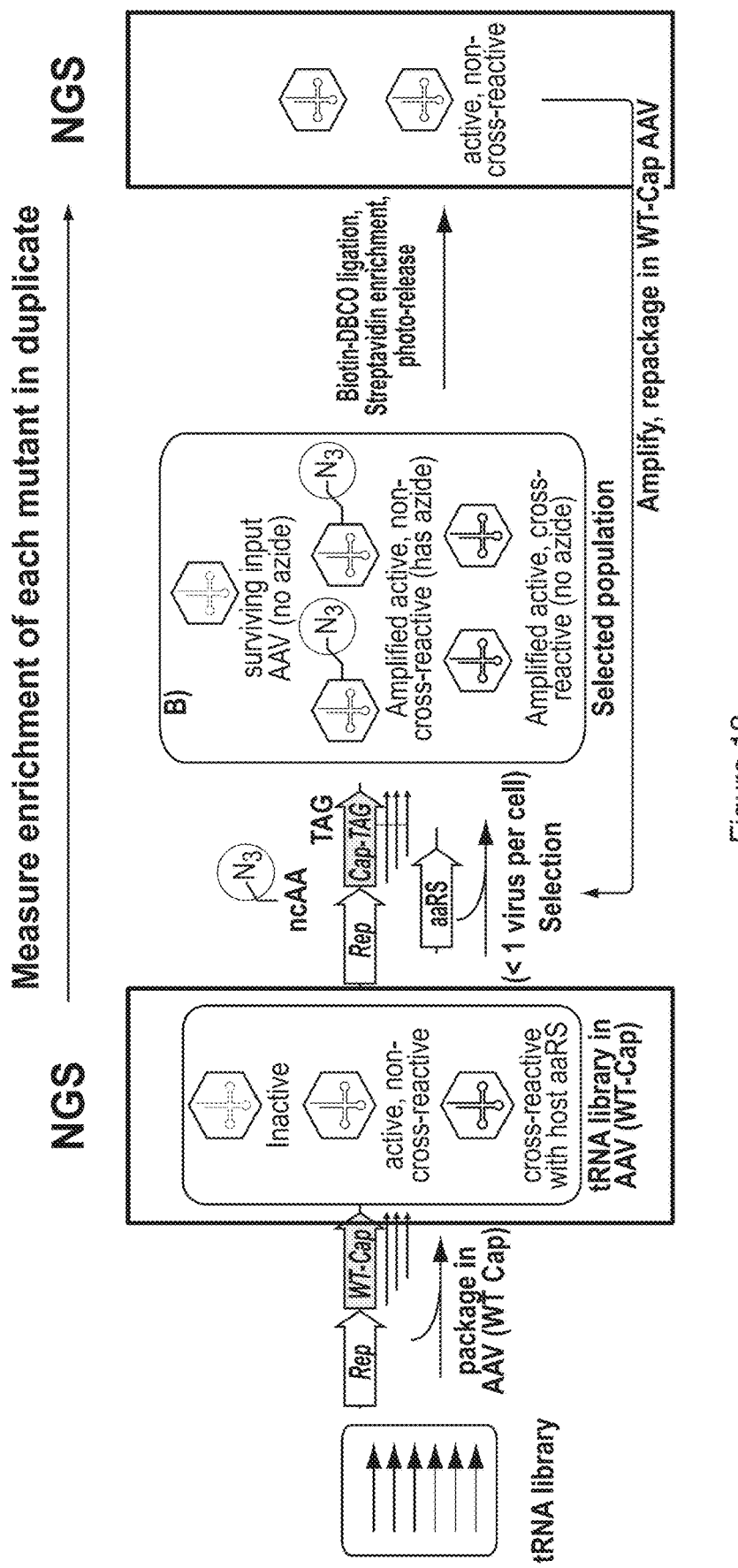
FIG. 12 shows the results of using next-generation Illumina DNA sequencing (NGS) to characterize the degree of enrichment for each mutant in a tRNA library, when subjected to VADER selection scheme. The resulting enrichment factors can be used to estimate the efficiency of the corresponding tRNA.
Figure 13:
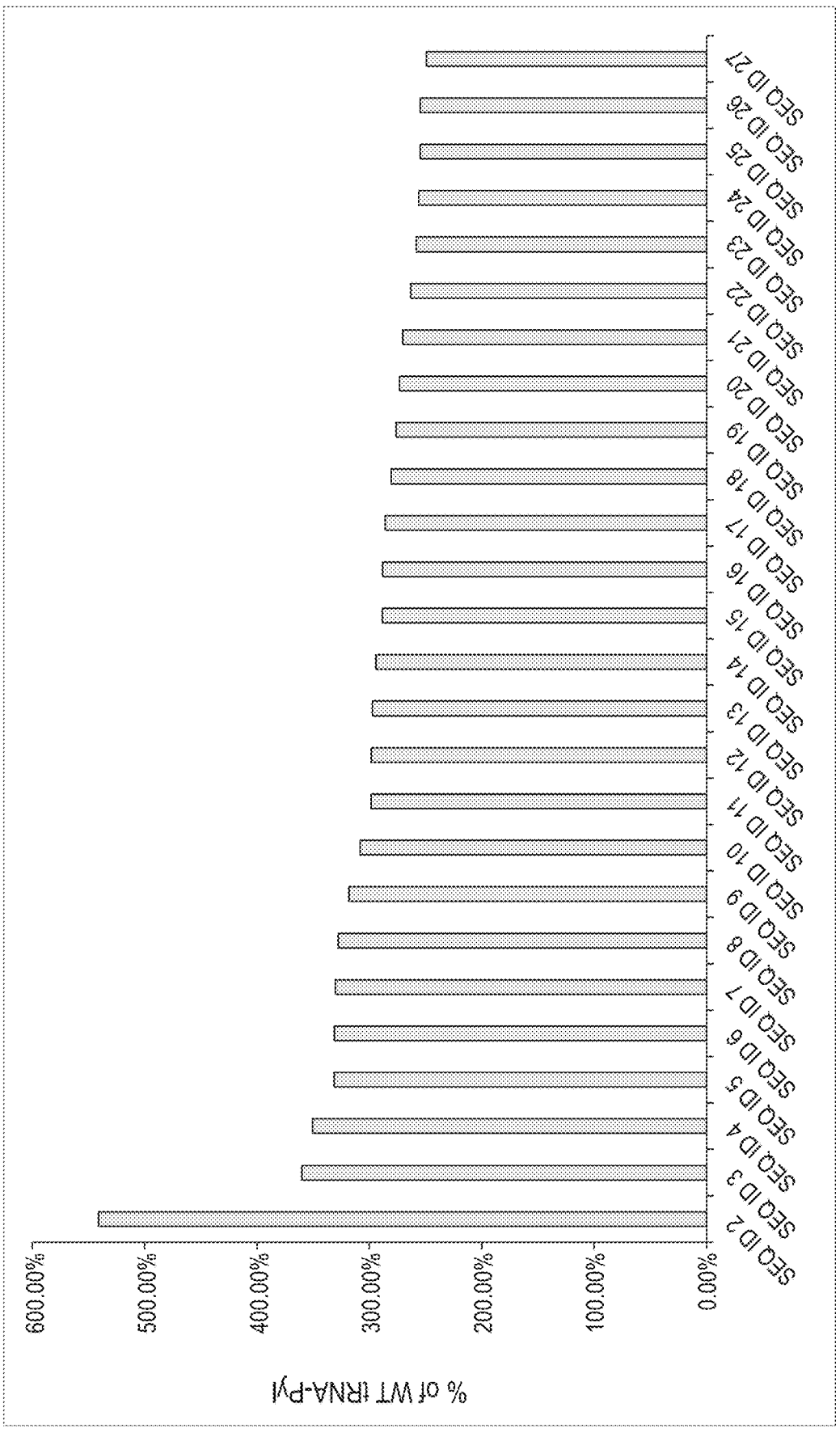
FIG. 13 shows the results of evaluation assays for improved activity of selected tRNA-Pyl mutants demonstrated using the expression of EGFP-39TAG reporter in HEK293T cells (as described earlier), normalized relative to wild-type mCherry expression, and plotted as a percentage of the reporter expression facilitated by wild-type tRNA-Pyl.

Using the DNA synthesis service provider TWIST bioscience, a pyrrolysyl-tRNA library was created as depicted in the FIG. 11, where six base pairs in the acceptor stem were randomized to desired combinations of base-pairing sequences. The resulting library was packaged in AAV2 and was subjected to the VADER selection scheme in duplicate as described above. The AAV2-packaged library was sequenced using Illumina platform for next generation sequencing before and after subjecting it to VADER selection (FIG. 12). The enrichment of each mutant was calculated using its abundance before and after the selection step and the mutants were ranked based on the degree of enrichment. The mutants that exhibited the highest degree of enrichment upon selection were resynthesized and their activities were benchmarked using the EGFP-39-TAG expression assay as described before (FIG. 13). As shown in FIG. 13, 26 tRNA-Pyl mutants demonstrated activity that was at least 250% higher relative to wild-type tRNA-Pyl, with the most active mutant demonstrating 540% activity relative to WT-tRNA-Pyl.

Figure 14A:
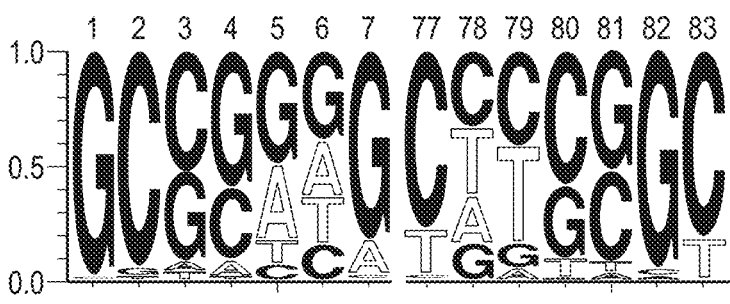
FIG. 14*a-b* The top panel (14*a*) shows the compiled sequences of the acceptor stem region of 120 different bacterial leucyl-tRNAs in the Weblogo format (https://weblogo.berkeley.edu/). In this format, the relative abundance of a particular nucleotide found at a particular position within this set of tRNA sequences is represented by the relative height of the corresponding letter code. The bottom panel (14*b*) shows the sequence and the secondary structure of the wild-type *E. coli* leucyl-tRNA (SEQ ID NO: 49/SEQ ID NO:28), and further shows the custom randomization targeted to each position in the acceptor stem guided by the sequence alignment.
Figure 14B:
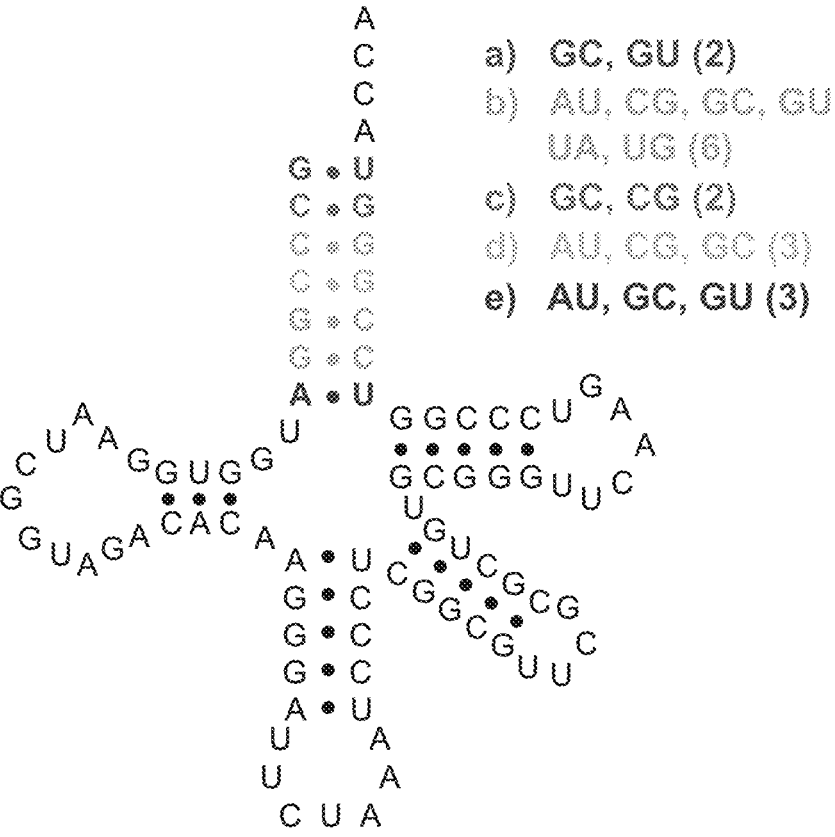
Figure 15:
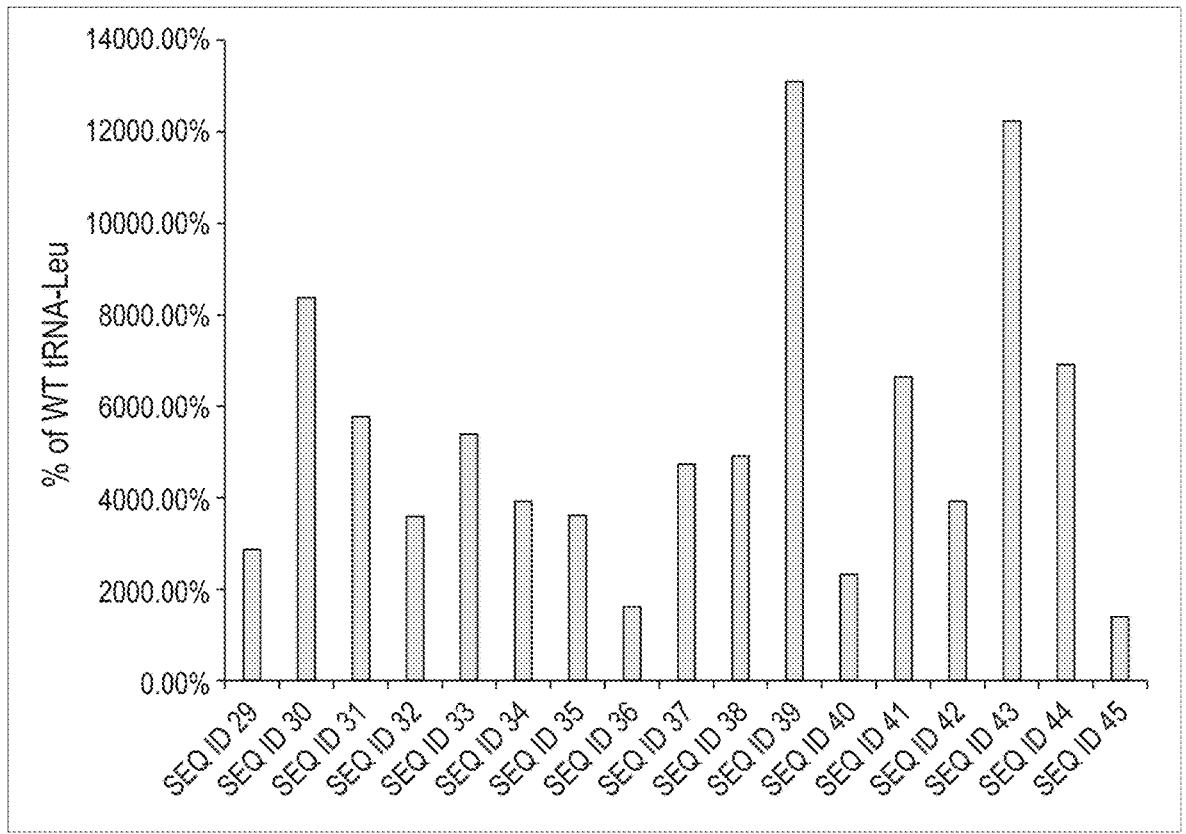
FIG. 15 shows the results of evaluation assays for improved activity of selected tRNA-Leu mutants demonstrated using the expression of EGFP-39717AG reporter in HEK293T cells (as described earlier), normalized relative to wild-type mCherry expression, and plotted as a percentage of the reporter expression facilitated by wild-type tRNA-Leu.

Example 7: Evolution of *E. coli* Leucyl-tRNA for
Enhanced Nonsense Suppression Activity in
Mammalian Cells Application of the VADER selection scheme for engineering tRNA activity in mammalian cells is not restricted only to the pyrrolysyl tRNA. It can be used to also improve the activity of other tRNAs that are suitable for Uaa. incorporation in mammalian cells. The use of the VADER methodology described herein was also used to improve the activity of *E. coli* leucyl tRNA (tRNA-Leu), which along with its cognate *E. coli* leucyl-tRNA synthetase (EcLeuRS) has been previously used for Uaa incorporation in mammalian cells (*J. Am. Chem. Soc.* 2004, 126, 14306; *Biochemistry* 2018, 57, 441). As shown with the work described herein on the tRNA-Pyl, engineering the acceptor stem is often very attractive, as this region interfaces with many components of the translation system. To design a 'smart' library, the sequences of 120 known bacterial tRNA sequences were aligned to generate a consensus sequence of the acceptor stem (FIG. 14). This consensus sequence could be used as a guide to predict which parts of the acceptor stem may be important in tRNA-aaRS interaction (identity element), and which regions offer room for alteration. Based on this approach, a custom-randomization library of the tRNA-Leu acceptor stem (FIG. 14) was designed. This library was packaged in AAV2 and subjected to VADER selection scheme as described above. A previously developed polyspecific EcLeuRS mutant (*Biochemistry* 2018, 57, 441), that can charge the azido-containing (azido-modified) Uaa AzK was used in the VADER scheme to charge the tRNA mutants. Next-generation Illumina DNA sequencing was used to measure the enrichment of each library member before and after the selection, as described above, and the ones exhibiting the most enrichment were resynthesized and characterized using the previously described EGFP-39-TAG reporter expression assay. As shown in FIG. 15, seventeen tRNA-Leu mutants demonstrated activity that was at least 1,000% higher relative to wild-type tRNA-Leu, with the most active mutant demonstrating approximately 13,000% enhanced activity relative to WT-tRNA-Leu. These tRNA sequences, including WT-tRNA-Leu, contains U at the 33 position, the first nucleotide in the anticodon loop. Mutation of this U to C can result in enhanced nonsense suppression activity, as it typically provides a better context for the nonsense suppressor anticodon. To find out if this is the case, the 33-U to C in mutant 29 (SEQ ID NO: 29) was mutated to create mutant 30 (SEQ ID NO: 30). Indeed, this mutant shows significantly improved suppression activity relative to 29 (FIG. 15). Introducing this mutation to other identified tRNA-Leu mutants (SEQ ID NOS: 31-45) should also result in an further improvement of their activity.

Example 8: The Engineered tRNA Mutants Show Further Improvement Relative to Their Wild-Type Counterparts when Their Expression Levels are Controlled Limited So far, all evaluation of all tRNA activities were performed by transient transfection of plasmids encoding the tRNA, aaRS, and the reporter into mammalian cells. It is well-established that transient transfection of mammalian cell culture results in an uncontrolled and heterogeneous level of DNA delivery, such that some of the cells uptake and overexpress the associated plasmids at a very high level, while others do not. It was previously demonstrated that the resulting overexpression of the encoding tRNA and aaRS can compensate for their poor intrinsic activity and inflate the estimate of their inherent efficiency (*ACS Synth. Bial.* 2017, 6, 13). It is further demonstrated as described herein, hat, as a result, comparing two different Uaa incorporation systems by transient transfection may yield an inaccurate estimate, where the efficiency of the weaker system is overestimated. It was surmised that the difference in efficiency observed using the transient-transfection assay might be underestimating the actual degree of improvement of inherent efficiency of different tRNA mutants relative to their wild-type counterparts.

Figure 16A:
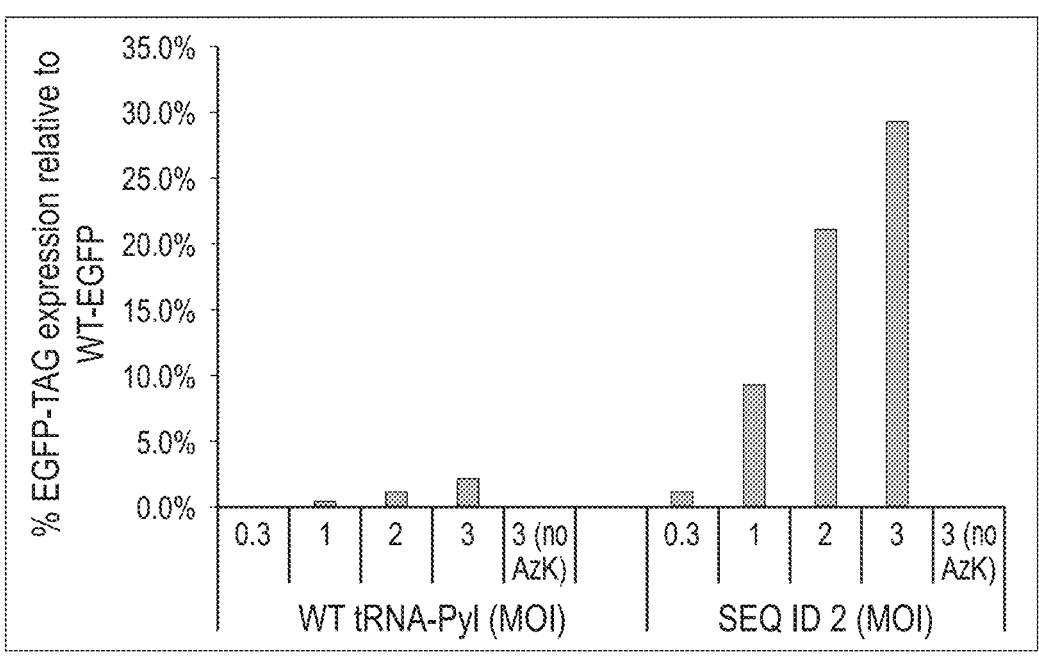
FIG. 16*a-b* shows the results of comparing the activities of WT tRNA-Pyl and tRNA-Pyl-2 (SEQ ID NO: 2) under controlled tRNA expression through baculovirus delivery. HEK293T cells were transduced with a baculovirus encoding MbPylRS and EGFP-39-TAG with a fixed MOI of 1, along with an increasing MOI (0.3 to 3) of a second baculovirus encoding an mCherry reporter and either the WT or engineered (SEQ ID NO: 2) tRNA-Pyl. All expressions except the no-AzK control are performed in the presence of 1 mM AzK, an Uaa substrate for MbPylRS. Expression of the mCherry is shown in the bottom panel, which increases linearly as increasing MOI of tRNA-mCherry virus is used and is comparable for WT and engineered tRNA-Pyl virus at the same MOI. The top panel shows EGFP-39-TAG expression relative to an identical virus encoding wild-type EGFP at the same MOI. The engineered tRNA-Pyl facilitates EGF-39-TAG expression at a much lower expression level (lower MOI) relative to the WT tRNA-Pyl.
Figure 16B:
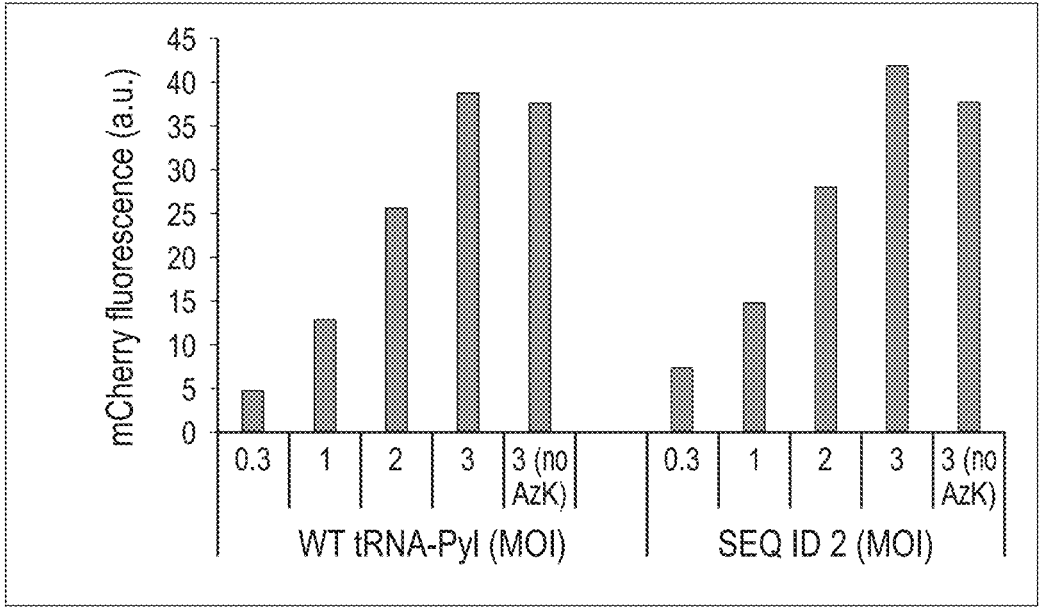
Figure 17A:
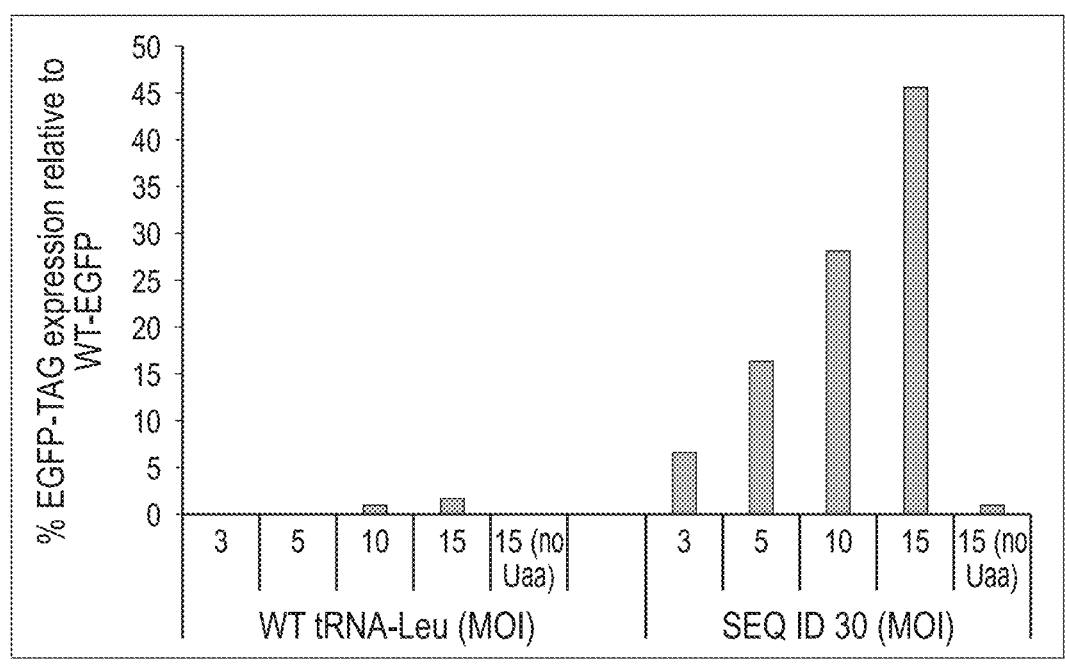
FIG. 17*a-b* shows the results of comparing the activities of WT tRNA-Leu and tRNA-Leu-30 (SEQ ID NO: 30) under controlled tRNA expression through baculovirus delivery. HEK293T cells were transduced with a baculovirus encoding EcLeuRS and EGFP-39-TAG with a fixed MOI of 1, along with an increasing MOI (3 to 15) of a second baculovirus encoding an mCherry reporter and either the WT or engineered (SEQ ID NO: 30) tRNA-Leu. All expressions except the no-Uaa control are performed in the presence of 1 mM Cap, a Uaa substrate for EcLeuRS. Expression of the mCherry reporter is shown in the bottom panel, which increases linearly as increasing MOI of tRNA-mCherry virus is used and is comparable for WT and engineered tRNA-Leu virus at the same MOI. The top panel shows EGFP-39-TAG expression relative to an identical virus encoding wild-type EGFP at the same MOI. The engineered tRNA-Leu facilitates EGF-39-TAG expression at a much lower expression level (lower MOI) relative to the WT tRNA-Leu.
Figure 17B:
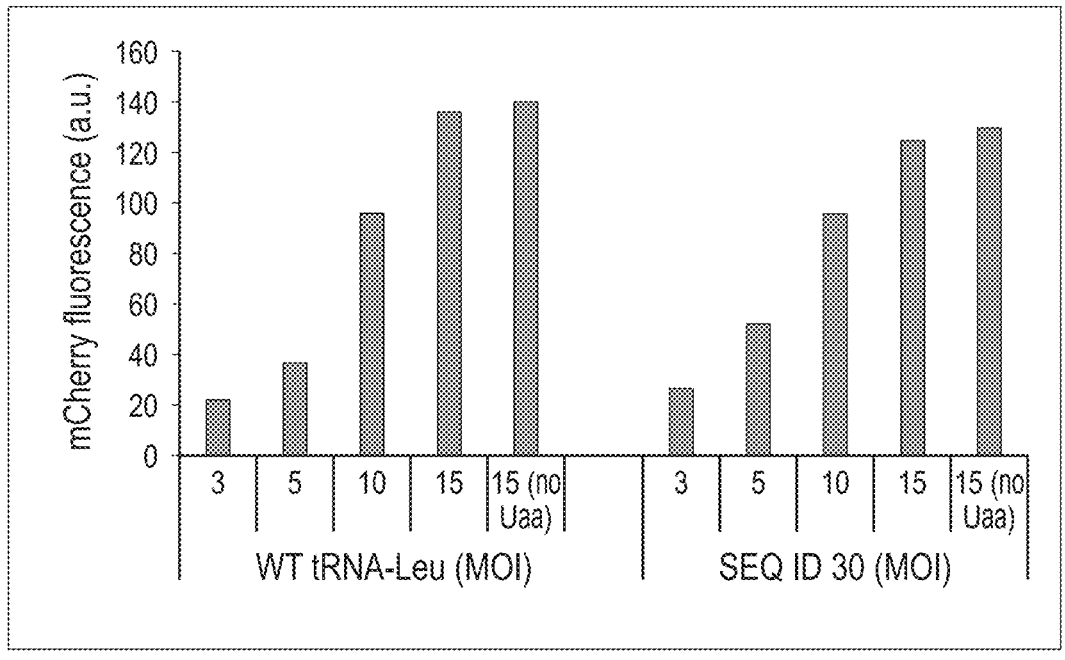

To overcome this challenge, a previously developed a baculovirus vector that facilitates controlled and more homogeneous delivery of transgenes to mammalian cells (*ACS Synth. Biol.* 2017, 6, 13) was used. The expression level of the transgene can be simply controlled by systematically altering the virus-to-cell ratio. Using this delivery system, it is possible to compare two different genetic systems for Uaa incorporation across a large spectrum of different expression levels, which more accurately reveals differences in their intrinsic performance. To compare the activity of the engineered tRNA-Pyl and tRNA-Leu mutants relative to their wild-type counterparts using this approach, baculovirus vectors were constructed that encode a wild-type mCherry reporter, as well as one of the four tRNAs: WT tRNA-Pyl, WT-tRNA-Leu, tRNA-Pyl-2 (SEQ ID 2), or tRNA-Leu-30 (SEQ ID 30). A second baculovirus was developed to deliver an EGFP-39-TAG reporter, as well as the necessary aaRS (MbPylRS for tRNA-Pyl, or EcLeuRS for tRNA-Leu). HEK293T cells were transduced with the aaRS/EGFP-39-TAG baculovirus with a fixed MOI (multiplicity of infection, or number of infective virus particles added per cell) of 1, along with an increasing MOI (0.3 to 15) of either the WT or engineered tRNA virus. Expression of the mCherry (confirming the delivery of the tRNA-baculovirus at desired level) and the EGFP-39-TAG (representing the Uaa incorporation efficiency in response to TAG) were recorded 48 hours post-transfection using their characteristic fluorescence in cell-free extract. As shown in FIG. 16, the engineered tRNA-Pyl facilitates EGF-39-TAG expression at a much lower expression level (lower MOI) relative to the WT tRNA-Pyl. For example, when WT tRNA-Pyl virus is used at MOI 1, expression of EGFP-39-TAG is only 0.5% with respect to the wild-type EGFP control; while the virus encoding engineered tRNA-Pyl (SEQ ID NO: 2) affords 9.3% EGFP-39-TAG expression at the same MOI, indicating a >18 fold higher efficiency of the latter at this expression level. At a higher MOI of 3, the engineered tRNA show approximately 14 fold higher activity relative to wild-type, underscoring how higher expression can underestimate true differences in intrinsic activity. We also compared the activities of wild-type tRNA-Leu and one of its engineered counterparts (SEQ ID NO: 30) in the same manner. As shown in FIG. 17, the engineered tRNA provide nearly 29-fold improved EGFP-39-TAG expression at the highest MOI tested (15). When the tRNAs were expressed at a lower level, the difference was even more stark; e.g., at MOI 5, the WT tRNA-Leu affords no detectable EGFP-39-TAG expression, while the tRNA-Leu-30 allows its expression at a 16% level relative to the wild-type reporter. That the engineered tRNAs provide significantly higher efficiency at lower expression levels is highly significant, since this will make it significantly easier to generate stable mammalian cell-lines with genomically integrated aaRS/tRNA that provide high Uaa incorporation efficiency.

Figure 18:
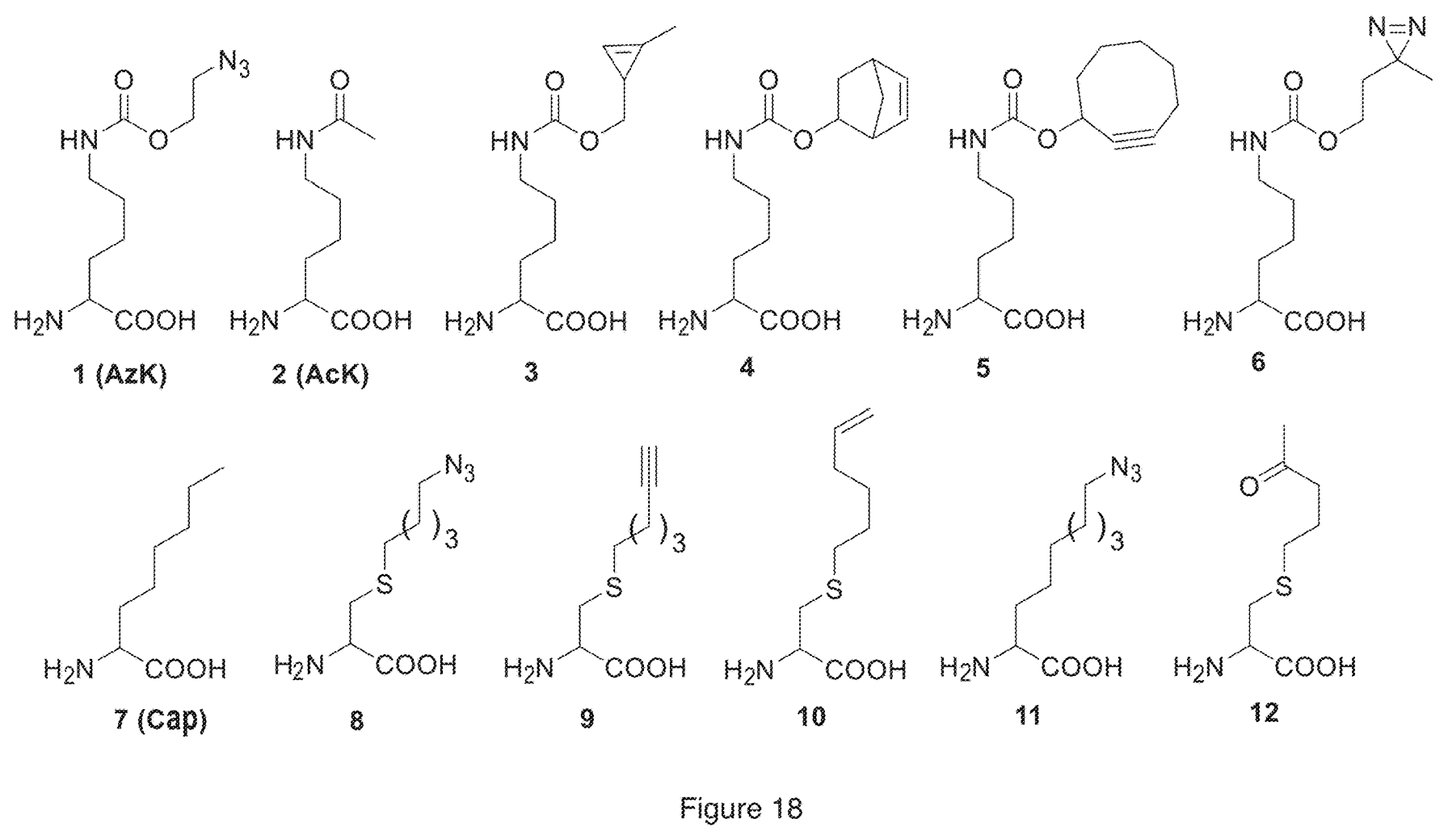
Figure 19A:
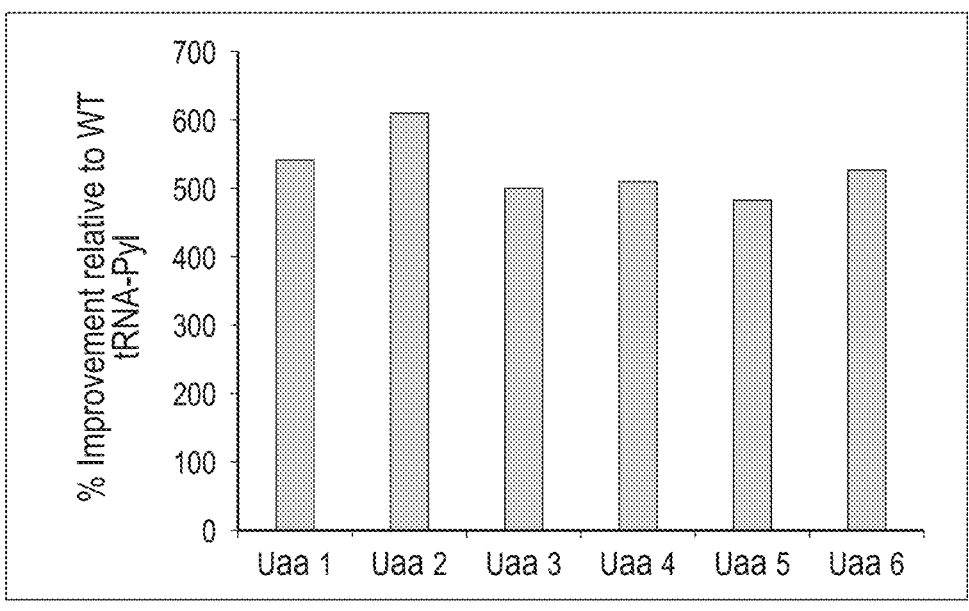
FIG. 19a-b shows the results of assays evaluating the improved tRNA-Pyl (SEQ ID NO: 2; top panel) and tRNA-Leu (SEQ ID NO: 30; bottom panel) facilitates more efficient incorporation of various Uaas shown FIG. 18.
Figure 19B:
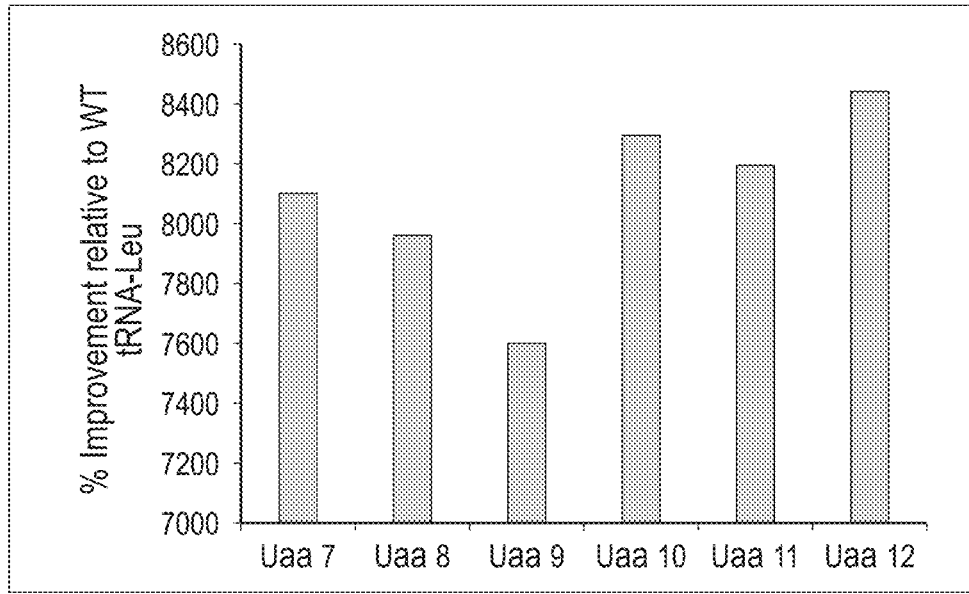

Example 9: The Engineered tRNA Mutants More Efficient Incorporation of Numerous Uaas Without being hound by theory, although the improved activity of the engineered tRNAs is not fully understood, it is likely that these interface with the mammalian translation system much better than their wild-type counterparts, which are borrowed from a different domain of life. Consequently, the improved activity of these tRNAs should enable more efficient incorporation of all Uaas which can be incorporated by an engineered mutant of its cognate aaRS. In order to demonstrate this hypothesis, several Uaas that can be incorporated using engineered MbPylRS (structures 1-6; FIG. 18) or EcLeuRS (structures 7-12; FIG. 18) were evaluated for their incorporation efficiency using the aforementioned EGFP-39-TAG expression assay. Indeed, each of these Uaas were incorporated by the engineered tRNAs at a significantly higher efficiency into the reporter by the two engineered tRNAs relative to their wild-type counterparts (FIG. 19).

While this invention has been particularly shown and described with references to preferred embodiments thereof, it will be understood by those skilled in the art that various changes in form and details may be made therein without departing from the scope of the invention encompassed by the appended claims.

What is claimed is:

1. A composition comprising a variant archaeal or variant bacterial suppressor tRNA, wherein the variant tRNA has increased activity relative to its wild-type counterpart tRNA to incorporate an unnatural amino acid into a protein produced in mammalian cells, wherein the activity of the variant tRNA is increased over the wild-type tRNA by about 10 to 80-fold.

2. The composition of claim 1, wherein the variant archaeal tRNA is a pyrrolysyl tRNA (tRNA$^{Pyl}$), and the tRNA$^{Pyl}$ comprises a nucleic acid sequence selected from the group consisting of: SEQ ID NOS: 2-27, or a nucleic acid sequence with at least 90% sequence identity with the full-length sequence of any of SEQ ID NOS: 2-27.

3. The composition of claim 1, wherein the variant bacterial tRNA is a leucyl tRNA (tRNA$^{Leu}$), and the tRNA$^{Leu}$ comprises a nucleic acid sequence selected from the group consisting of SEQ ID NOS: 29-45, or a nucleic acid sequence with at least 90% sequence identity with the full-length sequence of any of SEQ ID NOS: 29-45.

4. A viral vector comprising the composition of claim 1.

5. A cell comprising the viral vector of claim 4.

6. The cell of claim 5, wherein the cell is a mammalian cell.

7. The mammalian cell of claim 6, wherein the cell further comprises plasmids encoding:
   a) a protein essential for viral replication, wherein a nonsense codon is inserted into the protein sequence rendering viral replication dependent on the activity of the variant suppressor tRNA;
   b) a cognate Uaa RNA Synthetase (UaaRS); and
   c) genetic components required for viral replication.

8. An engineered mammalian cell with a stably integrated variant tRNA-Pyl for Uaa incorporation, wherein the variant tRNA-Pyl comprises the composition of claim 2.

9. The engineered mammalian cell of claim 8, wherein the cell comprises less than 250, 200, 150, 100, 75, 50 copies of a gene encoding the variant suppressor tRNA capable of incorporating an unnatural amino acid into a protein of interest.

10. The cell of claim 8, wherein the variant tRNA-Pyl is selected from the group consisting of SEQ ID NOS: 2-27 and the Uaa is a pyrrolysine analog.

11. The cell of claim 10, wherein the pyrrolysine analog is any of structures 1-6.

12. A viral vector comprising the composition of claim 2.

13. A cell comprising the viral vector of claim 12.

14. The cell of claim 13, wherein the cell is a mammalian cell.

15. The mammalian cell of claim 14, wherein the cell further comprises plasmids encoding:
   a) a protein essential for viral replication, wherein a nonsense codon is inserted into the protein sequence rendering viral replication dependent on the activity of the variant suppressor tRNA;
   b) a cognate Uaa RNA Synthetase (UaaRS); and
   c) genetic components required for viral replication.

16. An engineered mammalian cell with a stably integrated variant tRNA-Leu for Uaa incorporation, wherein the variant tRNA-Leu comprises the composition of claim 3.

17. The engineered mammalian cell of claim 16, wherein the cell comprises less than 250, 200, 150, 100, 75, 50 copies of a gene encoding the variant suppressor tRNA capable of incorporating an unnatural amino acid into a protein of interest.

18. The cell of claim 17, wherein the variant tRNA-Leu is selected from the group consisting of SEQ ID NOS: 29-45 and the Uaa is a leucine analog.

19. The cell of claim 18, wherein the leucine analog is any of structures 7-12.

20. A viral vector comprising the composition of claim 3.

21. A cell comprising the viral vector of claim 20.

22. The cell of claim 21, wherein the cell is a mammalian cell.

23. The mammalian cell of claim 22, wherein the cell further comprises plasmids encoding:
   a) a protein essential for viral replication, wherein a nonsense codon is inserted into the protein sequence rendering viral replication dependent on the activity of the variant suppressor tRNA;
   b) a cognate Uaa RNA Synthetase (UaaRS); and
   c) genetic components required for viral replication.

* * * * *

SEQUENCE LISTING

```
<160> NUMBER OF SEQ ID NOS: 49

<210> SEQ ID NO 1
<211> LENGTH: 72
<212> TYPE: RNA
<213> ORGANISM: Methanosarcina barkeri

<400> SEQUENCE: 1
ggaaaccuga ucauguagau cgaacggacu cuaaauccgu ucagccgggu uagauucccg      60
ggguuuccgc ca                                                          72

<210> SEQ ID NO 2
<211> LENGTH: 72
<212> TYPE: RNA
<213> ORGANISM: Methanosarcina barkeri

<400> SEQUENCE: 2
gggcggcuga ucauguagau cgaacggacu cuaaauccgu ucagccgggu uagauucccg      60
ggcugcccgc ca                                                          72

<210> SEQ ID NO 3
<211> LENGTH: 72
<212> TYPE: RNA
<213> ORGANISM: Methanosarcina barkeri

<400> SEQUENCE: 3
gggugacuga ucauguagau cgaacggacu cuaaauccgu ucagccgggu uagauucccg      60
gguugcccgc ca                                                          72

<210> SEQ ID NO 4
<211> LENGTH: 72
<212> TYPE: RNA
<213> ORGANISM: Methanosarcina barkeri

<400> SEQUENCE: 4 gggggcuga ucauguagau cgaacggacu cuaaauccgu ucagccgggu uagauucccg       60
ggcuccccgc ca                                                          72

<210> SEQ ID NO 5
<211> LENGTH: 72
<212> TYPE: RNA
<213> ORGANISM: Methanosarcina barkeri

<400> SEQUENCE: 5
gggcggcuga ucauguagau cgaacggacu cuaaauccgu ucagccgggu uagauucccg      60
gguugcccgc ca                                                          72

<210> SEQ ID NO 6
<211> LENGTH: 72
<212> TYPE: RNA
<213> ORGANISM: Methanosarcina barkeri

<400> SEQUENCE: 6
gggcgccuga ucauguagau cgaacggacu cuaaauccgu ucagccgggu uagauucccg      60
gggcgcccgc ca                                                          72

<210> SEQ ID NO 7
<211> LENGTH: 72
<212> TYPE: RNA
<213> ORGANISM: Methanosarcina barkeri
```

-continued

<400> SEQUENCE: 7
ggggagguga ucauguagau cgaacggacu cuaaauccgu ucagccgggu uagauucccg      60
gccuccccgc ca      72

<210> SEQ ID NO 8
<211> LENGTH: 72
<212> TYPE: RNA
<213> ORGANISM: Methanosarcina barkeri

<400> SEQUENCE: 8
ggggaccuga ucauguagau cgaacggacu cuaaauccgu ucagccgggu uagauucccg      60
ggguccccgc ca      72

<210> SEQ ID NO 9
<211> LENGTH: 72
<212> TYPE: RNA
<213> ORGANISM: Methanosarcina barkeri

<400> SEQUENCE: 9
ggccggguga ucauguagau cgaacggacu cuaaauccgu ucagccgggu uagauucccg      60
gccuggccgc ca      72

<210> SEQ ID NO 10
<211> LENGTH: 72
<212> TYPE: RNA
<213> ORGANISM: Methanosarcina barkeri

<400> SEQUENCE: 10
ggggaccuga ucauguagau cgaacggacu cuaaauccgu ucagccgggu uagauucccg      60
ggguccucgc ca      72

<210> SEQ ID NO 11
<211> LENGTH: 72
<212> TYPE: RNA
<213> ORGANISM: Methanosarcina barkeri

<400> SEQUENCE: 11
ggggcccuga ucauguagau cgaacggacu cuaaauccgu ucagccgggu uagauucccg      60
ggggucccgc ca      72

<210> SEQ ID NO 12
<211> LENGTH: 72
<212> TYPE: RNA
<213> ORGANISM: Methanosarcina barkeri

<400> SEQUENCE: 12
gggggccuga ucauguagau cgaacggacu cuaaauccgu ucagccgggu uagauucccg      60
gggcucccgc ca      72

<210> SEQ ID NO 13
<211> LENGTH: 72
<212> TYPE: RNA
<213> ORGANISM: Methanosarcina barkeri

<400> SEQUENCE: 13
gggguccuga ucauguagau cgaacggacu cuaaauccgu ucagccgggu uagauucccg      60
gggaucccgc ca      72

<210> SEQ ID NO 14
<211> LENGTH: 72
<212> TYPE: RNA
<213> ORGANISM: Methanosarcina barkeri

<400> SEQUENCE: 14
ggggaccuga ucauguagau cgaacggacu cuaaauccgu ucagccgggu uagauucccg      60
ggguucccgc ca                                                         72

<210> SEQ ID NO 15
<211> LENGTH: 72
<212> TYPE: RNA
<213> ORGANISM: Methanosarcina barkeri

<400> SEQUENCE: 15
ggggagguga ucauguagau cgaacggacu cuaaauccgu ucagccgggu uagauucccg      60
gucuucccgc ca                                                         72

<210> SEQ ID NO 16
<211> LENGTH: 72
<212> TYPE: RNA
<213> ORGANISM: Methanosarcina barkeri

<400> SEQUENCE: 16
ggggggguga ucauguagau cgaacggacu cuaaauccgu ucagccgggu uagauucccg      60
gcccccucgc ca                                                         72

<210> SEQ ID NO 17
<211> LENGTH: 72
<212> TYPE: RNA
<213> ORGANISM: Methanosarcina barkeri

<400> SEQUENCE: 17
ggugggguga ucauguagau cgaacggacu cuaaauccgu ucagccgggu uagauucccg      60
gcccuaccgc ca                                                         72

<210> SEQ ID NO 18
<211> LENGTH: 72
<212> TYPE: RNA
<213> ORGANISM: Methanosarcina barkeri

<400> SEQUENCE: 18 ggggucuga ucauguagau cgaacggacu cuaaauccgu ucagccgggu uagauucccg      60 ggacuccgc ca                                                         72

<210> SEQ ID NO 19
<211> LENGTH: 72
<212> TYPE: RNA
<213> ORGANISM: Methanosarcina barkeri

<400> SEQUENCE: 19
gggucccuga ucauguagau cgaacggacu cuaaauccgu ucagccgggu uagauucccg      60
ggggguccgc ca                                                         72

<210> SEQ ID NO 20
<211> LENGTH: 72
<212> TYPE: RNA
<213> ORGANISM: Methanosarcina barkeri -continued

```
<400> SEQUENCE: 20
ggggaccuga ucauguagau cgaacggacu cuaaauccgu ucagccgggu uagauucccg      60
ggguucucgc ca                                                         72

<210> SEQ ID NO 21
<211> LENGTH: 72
<212> TYPE: RNA
<213> ORGANISM: Methanosarcina barkeri

<400> SEQUENCE: 21
gggcggcuga ucauguagau cgaacggacu cuaaauccgu ucagccgggu uagauucccg      60
ggccgcccgc ca                                                         72

<210> SEQ ID NO 22
<211> LENGTH: 72
<212> TYPE: RNA
<213> ORGANISM: Methanosarcina barkeri

<400> SEQUENCE: 22
gagcaccuga ucauguagau cgaacggacu cuaaauccgu ucagccgggu uagauucccg      60
gggugcucgc ca                                                         72

<210> SEQ ID NO 23
<211> LENGTH: 72
<212> TYPE: RNA
<213> ORGANISM: Methanosarcina barkeri

<400> SEQUENCE: 23
ggggggguga ucauguagau cgaacggacu cuaaauccgu ucagccgggu uagauucccg      60
gcccccccgc ca                                                         72

<210> SEQ ID NO 24
<211> LENGTH: 72
<212> TYPE: RNA
<213> ORGANISM: Methanosarcina barkeri

<400> SEQUENCE: 24
gaggggguga ucauguagau cgaacggacu cuaaauccgu ucagccgggu uagauucccg      60
gcccccucgc ca                                                         72

<210> SEQ ID NO 25
<211> LENGTH: 72
<212> TYPE: RNA
<213> ORGANISM: Methanosarcina barkeri

<400> SEQUENCE: 25
gggagccuga ucauguagau cgaacggacu cuaaauccgu ucagccgggu uagauucccg      60
ggguucccgc ca                                                         72

<210> SEQ ID NO 26
<211> LENGTH: 72
<212> TYPE: RNA
<213> ORGANISM: Methanosarcina barkeri

<400> SEQUENCE: 26
gggagccuga ucauguagau cgaacggacu cuaaauccgu ucagccgggu uagauucccg      60
ggguucccgc ca                                                         72
```

-continued

<210> SEQ ID NO 27
<211> LENGTH: 72
<212> TYPE: RNA
<213> ORGANISM: Methanosarcina barkeri

<400> SEQUENCE: 27
gaggaccuga ucauguagau cgaacggacu cuaaauccgu ucagccgggu uagauucccg      60
ggguucucgc ca                                                        72

<210> SEQ ID NO 28
<211> LENGTH: 87
<212> TYPE: RNA
<213> ORGANISM: Escherichia coli

<400> SEQUENCE: 28
gcccggaugg uggaaucggu agacacaagg gauucuaaau cccucggcgu ucgcgcugug      60
cggguucaag ucccgcuccg gguacca                                        87

<210> SEQ ID NO 29
<211> LENGTH: 87
<212> TYPE: RNA
<213> ORGANISM: Escherichia coli

<400> SEQUENCE: 29
gcccggaugg uggaaucggu agacacaagg gauucuaaau cccucggcgu ucgcgcugug      60
cggguucaag ucccgcuccg ggcacca                                        87

<210> SEQ ID NO 30
<211> LENGTH: 87
<212> TYPE: RNA
<213> ORGANISM: Escherichia coli

<400> SEQUENCE: 30
gcccggaugg uggaaucggu agacacaagg gacucuaaau cccucggcgu ucgcgcugug      60
cggguucaag ucccgcuccg ggcacca                                        87

<210> SEQ ID NO 31
<211> LENGTH: 87
<212> TYPE: RNA
<213> ORGANISM: Escherichia coli

<400> SEQUENCE: 31
gggcgugugg uggaaucggu agacacaagg gauucuaaau cccucggcgu ucgcgcugug      60
cggguucaag ucccgccgcg cccacca                                        87

<210> SEQ ID NO 32
<211> LENGTH: 87
<212> TYPE: RNA
<213> ORGANISM: Escherichia coli

<400> SEQUENCE: 32
gggcgcgugg uggaaucggu agacacaagg gauucuaaau cccucggcgu ucgcgcugug      60
cggguucaag ucccgccgcg cccacca                                        87

<210> SEQ ID NO 33
<211> LENGTH: 87
<212> TYPE: RNA
<213> ORGANISM: Escherichia coli -continued

<400> SEQUENCE: 33
gggcaugugg uggaaucggu agacacaagg gauucuaaau cccucggcgu ucgcgcugug    60
cggguucaag ucccgccaug cccacca    87

<210> SEQ ID NO 34
<211> LENGTH: 87
<212> TYPE: RNA
<213> ORGANISM: Escherichia coli

<400> SEQUENCE: 34
gggcacgugg uggaaucggu agacacaagg gauucuaaau cccucggcgu ucgcgcugug    60
cggguucaag ucccgccgug cccacca    87

<210> SEQ ID NO 35
<211> LENGTH: 87
<212> TYPE: RNA
<213> ORGANISM: Escherichia coli

<400> SEQUENCE: 35
gggggugugg uggaaucggu agacacaagg gauucuaaau cccucggcgu ucgcgcugug    60
cggguucaag ucccgccgcc cccacca    87

<210> SEQ ID NO 36
<211> LENGTH: 87
<212> TYPE: RNA
<213> ORGANISM: Escherichia coli

<400> SEQUENCE: 36
gggggcgugg uggaaucggu agacacaagg gauucuaaau cccucggcgu ucgcgcugug    60
cggguucaag ucccgccguc cccacca    87

<210> SEQ ID NO 37
<211> LENGTH: 87
<212> TYPE: RNA
<213> ORGANISM: Escherichia coli

<400> SEQUENCE: 37
ggggaugugg uggaaucggu agacacaagg gauucuaaau cccucggcgu ucgcgcugug    60
cggguucaag ucccgccguc cccacca    87

<210> SEQ ID NO 38
<211> LENGTH: 87
<212> TYPE: RNA
<213> ORGANISM: Escherichia coli

<400> SEQUENCE: 38
ggggacgugg uggaaucggu agacacaagg gauucuaaau cccucggcgu ucgcgcugug    60
cggguucaag ucccgccguc cccacca    87

<210> SEQ ID NO 39
<211> LENGTH: 87
<212> TYPE: RNA
<213> ORGANISM: Escherichia coli

<400> SEQUENCE: 39
gcccguaugg uggaaucggu agacacaagg gauucuaaau cccucggcgu ucgcgcugug    60
cggguucaag ucccgcugcg ggcacca    87

<210> SEQ ID NO 40
<211> LENGTH: 87
<212> TYPE: RNA
<213> ORGANISM: Escherichia coli

<400> SEQUENCE: 40
gggauagugg uggaaucggu agacacaagg gauucuaaau cccucggcgu ucgcgcugug        60
cggguucaag ucccgccuau cccacca                                           87

<210> SEQ ID NO 41
<211> LENGTH: 87
<212> TYPE: RNA
<213> ORGANISM: Escherichia coli

<400> SEQUENCE: 41
gggcaugugg uggaaucggu agacacaagg gauucuaaau cccucggcgu ucgcgcugug        60
cggguucaag ucccgccgug cccacca                                           87

<210> SEQ ID NO 42
<211> LENGTH: 87
<212> TYPE: RNA
<213> ORGANISM: Escherichia coli

<400> SEQUENCE: 42
gggcagaugg uggaaucggu agacacaagg gauucuaaau cccucggcgu ucgcgcugug        60
cggguucaag ucccgcucug cccacca                                           87

<210> SEQ ID NO 43
<211> LENGTH: 87
<212> TYPE: RNA
<213> ORGANISM: Escherichia coli

<400> SEQUENCE: 43
gggcguaugg uggaaucggu agacacaagg gauucuaaau cccucggcgu ucgcgcugug        60
cggguucaag ucccgcugcg cccacca                                           87

<210> SEQ ID NO 44
<211> LENGTH: 87
<212> TYPE: RNA
<213> ORGANISM: Escherichia coli

<400> SEQUENCE: 44
gggcaagugg uggaaucggu agacacaagg gauucuaaau cccucggcgu ucgcgcugug        60
cggguucaag ucccgccuug cccacca                                           87

<210> SEQ ID NO 45
<211> LENGTH: 87
<212> TYPE: RNA
<213> ORGANISM: Escherichia coli

<400> SEQUENCE: 45
gcacacaugg uggaaucggu agacacaagg gauucuaaau cccucggcgu ucgcgcugug        60
cggguucaag ucccgcugug ugcacca                                           87

<210> SEQ ID NO 46
<211> LENGTH: 735
<212> TYPE: PRT
<213> ORGANISM: Adeno-associated virus - 2

<400> SEQUENCE: 46

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
                260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

-continued

```
Gln Met Leu Arg Thr Gly Asn Asn Phe Thr Phe Ser Tyr Thr Phe Glu
            405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
            435                 440                 445

Asn Thr Pro Ser Gly Thr Thr Thr Gln Ser Arg Leu Gln Phe Ser Gln
    450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
            485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
            515                 520                 525

Asp Glu Glu Lys Phe Phe Pro Gln Ser Gly Val Leu Ile Phe Gly Lys
    530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
            565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
            595                 600                 605

Arg Asp Val Tyr Leu Gln Gly Pro Ile Trp Ala Lys Ile Pro His Thr
    610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
            645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
            675                 680                 685

Glu Asn Ser Lys Arg Trp Asn Pro Glu Ile Gln Tyr Thr Ser Asn Tyr
    690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
            725                 730                 735
```

```
<210> SEQ ID NO 47
<211> LENGTH: 87
<212> TYPE: DNA
<213> ORGANISM: Escherichia coli

<400> SEQUENCE: 47
gcccggatgg tggaatcggt agacacaagg gattctaaat ccctcggcgt tcgcgctgtg        60
cgggttcaag tcccgctccg ggtacca                                            87

<210> SEQ ID NO 48
<211> LENGTH: 87
```

-continued

```
<212> TYPE: DNA
<213> ORGANISM: Escherichia coli

<400> SEQUENCE: 48
gcccggatgg tggaatcggt agacacaagg gactctaaat ccctcggcgt tcgcgctgtg        60
cgggttcaag tcccgctccg ggcacca                                            87

<210> SEQ ID NO 49
<211> LENGTH: 87
<212> TYPE: RNA
<213> ORGANISM: Escherichia coli

<400> SEQUENCE: 49
gcccggaugg uggaaucggu agacacaagg gauucuaaau cccucggcgu ucgcgcugug        60
cggguucaag ucccgguccg gguacca                                            87
```